(12) United States Patent
McPhail et al.

(10) Patent No.: US 9,359,323 B2
(45) Date of Patent: Jun. 7, 2016

(54) COMPOUND

(76) Inventors: Donald Barton McPhail, Aberdeen (GB); Graeme James Cook, Aberdeen (GB); Richard Charles Hartley, Glasgow (GB)

( * ) Notice: Subject to any disclaimer, the term of this patent is extended or adjusted under 35 U.S.C. 154(b) by 108 days.

(21) Appl. No.: 13/879,130

(22) PCT Filed: Oct. 13, 2011

(86) PCT No.: PCT/GB2011/001477
§ 371 (c)(1),
(2), (4) Date: Jun. 25, 2013

(87) PCT Pub. No.: WO2012/049460
PCT Pub. Date: Apr. 19, 2012

(65) Prior Publication Data
US 2013/0267586 A1    Oct. 10, 2013

(30) Foreign Application Priority Data

Oct. 13, 2010  (GB) .................................. 1017315.1

(51) Int. Cl.
    *C07D 311/00*   (2006.01)
    *C07D 315/00*   (2006.01)
    (Continued)

(52) U.S. Cl.
    CPC ............ *C07D 311/62* (2013.01); *C07D 309/40* (2013.01); *C07D 311/26* (2013.01)

(58) Field of Classification Search
    CPC ... C07D 309/40; C07D 311/62; C07D 311/26
    USPC ........... 514/456, 460; 435/375; 549/400, 418
    See application file for complete search history.

(56) References Cited

U.S. PATENT DOCUMENTS 5,280,024 A   1/1994  Bolland
5,702,691 A   12/1997 Ichinose
              (Continued)

FOREIGN PATENT DOCUMENTS

CA   2566166 A1   4/2008
EP   0743311 A1   11/1996
                 (Continued)

OTHER PUBLICATIONS

El-Desouky et al, A new pyranone derivative from the leaves of *Livistona australis*, 2009, Natural Product Communications, 4(4), p. 499-500, (abstract page).*

(Continued)

*Primary Examiner* — T. Victor Oh
(74) *Attorney, Agent, or Firm* — Law Office of Salvatore Arrigo and Scott Lee, LLP

(57) ABSTRACT

The present invention provides compounds of the formula Formula I or a salt thereof: and the uses of such compounds for the treatment of a disease or disorder involving oxidative damage, for preventing UV damage to the skin of a mammal and for preventing or reversing the effects of ageing, or for treating or preventing dry skin.

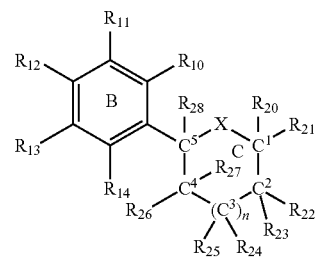

Formula I

11 Claims, 6 Drawing Sheets

(51) Int. Cl.
*C07D 311/62* (2006.01)
*C07D 309/40* (2006.01)
*C07D 311/26* (2006.01)

(56) References Cited

U.S. PATENT DOCUMENTS

| | | | |
|---|---|---|---|
| 5,912,174 | A | 6/1999 | Scheer |
| 6,080,780 | A | 6/2000 | Paladini |
| 7,601,754 | B2 | 10/2009 | Caldwell |
| 8,188,144 | B2 | 5/2012 | McPhail |
| 2005/0106554 | A1 | 5/2005 | Palecek |
| 2012/0094384 | A1 | 4/2012 | McPhail |

FOREIGN PATENT DOCUMENTS

| | | |
|---|---|---|
| EP | 1057405 B1 | 8/2004 |
| EP | 1627565 A1 | 2/2006 |
| EP | 1834952 A1 | 9/2007 |
| JP | 06161129 A | 6/1994 |
| JP | 2002255810 A | 11/2002 |
| WO | 0183469 A1 | 11/2001 |
| WO | 2004007475 A1 | 1/2004 |
| WO | 2005118785 A1 | 12/2005 |
| WO | 2006019366 A1 | 2/2006 |
| WO | 2008062184 A1 | 5/2008 |
| WO | 2009003229 A1 | 1/2009 |
| WO | 2009047568 A2 | 4/2009 |

OTHER PUBLICATIONS

International Search Report of PCT/GB2010/000722.
UK Search Report of GB0808715.7, dated Aug. 28, 2008.
Kim, Y. J., et al., Biochemical Pharmacology, vol. 72, No. 10, pp. 1268-1278 (2006).
"The Merck Index, 12th Ed.," 1996, Merk, Whitehouse Station, NJ, pp. 379, 475, 900, 1102, and 1381.
Tang, X., et al., Cell Biology International, vol. 30, No. 5, pp. 445-451 (2006).
Peng-Zhang et al., European Journal of Pharmacology, vol. 607, No. 1-3, pp. 1-5 (2009).
Zhu, D-Y, et al., ACTA Pharmacologica Sinica, vol. 26, No. 4, pp. 477-85 (2005).
Search Report in GB Application No. 1017315.1, Sep. 13, 2011.
ISR and Written Opinion in PCT/GB2011/001477, Dec. 9, 2011.
Abou El Hassan, M. A. I., et al., British Journal of Cancer, vol. 89, pp. 357-362 (2003).
Abou El Hassan, M. A. I., et al., British Journal of Cancer, vol. 89, pp. 2140-2146 (2003).
Bennett, C. J., et al., Bioorganic & Medicinal Chemistry, vol. 12, pp. 2079-98 (2004).
Chang, B. S., Kor. J. Pharmacogn., vol. 35, No. 1, pp. 80-87 (2004).
Li, C. et al., J. Agric. Food Chem., vol. 57, pp. 8496-8503 (2009).
Dangles, O., et al., J. Chem. Soc., Perkin Trans., vol. 2, pp. 1215-1222 (2000).
De Meyer, N., et al., J. Med. Chem. vol. 34, pp. 736-46 (1991).
Fukai, T. et al., Heterocycles, vol. 34, No. 6, pp. 1213-1226 (1992).
Kajiya, K. et al., J. Agric. Food Chem., vol. 52, pp. 1514-19 (2004).
Kamara, B. I., J. Agric. Food Chem., vol. 51, pp. 3874-79 (2003).
Kessler, M., et al., Journal of Pharmacy and Pharmacology, vol. 55, pp. 131-42 (2003).
Kim, S. R., et al., Free Radical Biology & Medicine, vol. 32, No. 7, pp. 596-604 (2002).
Kumar, M., et al., Fitoterapia, vol. 81, pp. 234-42 (2010).
Kwon, Y. S., et al., Arch. Pharm. Res., vol. 27, No. 7, pp. 751-56 (2004).
Miranda, C. L., et al., J. Agric. Food Chem., vol. 48, pp. 3876-84 (2000).
Paulo, A., et al., Phytotherapy Research, vol. 32, pp. 539-543 (2008).
Phan, T.-T., et al., Biol. Pharm. Bull., vol. 24, No. 12, pp. 1373-79 (2001).
Rice-Evans, C. A., et al., Free Radical Biology & Medicine, vol. 20, No. 7, pp. 933-956 (1996).
Sutthivaiyakit, S., et al., Tetrahedron, vol. 58, pp. 3619-3622 (2002).

* cited by examiner

A

B

A

B

COMPOUND

This application is the U.S. national stage of International Application No. PCT/GB2011/001477, filed Oct. 13, 2011, which claims the benefit of GB Application No. 1017315.1, filed Oct. 13, 2010, both of which are hereby incorporated herein by reference.

FIELD OF THE INVENTION

The present invention relates to novel antioxidant compounds and uses thereof.

BACKGROUND TO THE INVENTION

Antioxidant compounds are known in the art and have been used for various purposes.

WO 2004/007475 discloses the use of certain flavonoid compounds as antioxidants for the treatment of patients having a disease or disorder involving oxidative damage.

WO 2009/047568 discloses the use of certain flavonoid compounds in the in vitro preservation of living animal cells. The living animal cells may be isolated cells, such as stem cells, or groups of cells such as a tissue or organ.

SUMMARY OF THE INVENTION

The present inventors have identified novel antioxidant compounds.

In a first aspect, the present invention provides a compound of Formula I or a salt thereof:

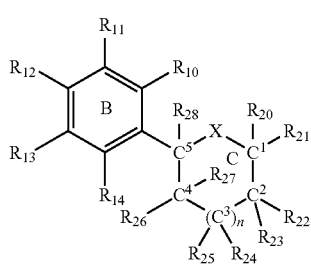

Formula I wherein:

A) X is —O—, —S— or —$NR_1$—, wherein $R_1$ i) represents H or $C_{1-6}$ alkyl, or ii) together with $R_{21}$ provides a second bond between $C^1$ and N;

B) $R_{12}$ represents —OH, a glycosidic functional group or =O; $R_{26}$ represents —OH, a glycosidic functional group or together with $R_{27}$ forms =O; $R_{10}$, $R_{11}$, $R_{13}$, and $R_{14}$ each independently represent H, —OH, =O, nitro, halogen, amino, amido, cyano, carboxyl, sulphonyl, a glycosidic functional group, $C_{1-6}$ alkoxy-, hydroxy-$C_{1-6}$ alkyl-, $C_{1-6}$ alkoxy-$C_{1-6}$ alkyl-, or a saturated or unsaturated $C_{1-6}$ hydrocarbon chain which may be substituted with one or more of nitro, halogen, amino, amido, cyano, carboxyl, sulphonyl, hydroxyl, ketone or aldehyde; and wherein Ring B comprises no more than one glycosidic functional group substituent and wherein the total number of =O on Ring B is no greater than 2;

C) either a):

$R_{20}$ represents H or a 3, 4, 5, 6, 7 or 8 membered saturated or unsaturated ring (hereinafter referred to as Ring D);

$R_{21}$:
i) represents H;
ii) together with $R_{22}$ provides a second bond between $C^1$ and $C^2$; or
iii) when X is —$NR_1$— and $R_1$ is not H or $C_{1-6}$ alkyl, $R_{21}$ together with $R_1$ provides a second bond between $C^1$ and N;

$R_{22}$:
i) represents H;
ii) together with $R_{23}$ forms =O; or
iii) together with $R_{21}$ provides a second bond between $C^1$ and $C^2$;

$R_{23}$:
i) represents H or a 3, 4, 5, 6, 7 or 8 membered saturated or unsaturated ring (Ring D); or
ii) together with $R_{22}$ forms =O;
wherein at least one of $R_{20}$ and $R_{23}$ is a 3, 4, 5, 6, 7 or 8 membered saturated or unsaturated ring (Ring D);

or b):

$R_{20}$, $R_{21}$, $R_{22}$, and $R_{23}$ form part of a 5, 6 or 7 membered unsaturated ring including $C^1$ and $C^2$, which ring (hereinafter referred to as Ring A) is substituted with at least one group;

said at least one group being a 3, 4, 5, 6, 7 or 8 membered saturated or unsaturated ring (Ring D); and wherein the ring formed by $R_{20}$, $R_{21}$, $R_{22}$, and $R_{23}$ (Ring A) is optionally and independently further substituted with one or more groups independently selected from —OH and a 3, 4, 5, 6, 7 or 8 membered saturated or unsaturated ring (Ring D);

wherein the ring formed by $R_{20}$, $R_{21}$, $R_{22}$, and $R_{23}$ (Ring A) and the 3, 4, 5, 6, 7 or 8 membered saturated or unsaturated ring (Ring D) are optionally and independently further substituted with one or more groups selected from an O—, S—, or N-containing functional group, for example, nitro, hydroxyl, carboxyl, ketone, amino, or thiol, or benzyl, phenyl, unsaturated 5, 6, 7 or 8 membered ring, cycloalkyl, cycloalkenyl, cycloalkynyl, amido, cyano, sulphonyl, aldehyde, nitrone, $C_2$-$C_6$ alkenyl, $C_2$-$C_6$ alkynyl, —$NH_2$, —F, $C_{1-6}$ alkoxy, hydroxy-$C_{1-6}$ alkyl, —$CO_2H$, —$CO_2C_{1-6}$alkyl, —$S(O)_2C_{1-6}$alkyl, —$S(O)_2$-phenyl, —$NO_2$, —OH, —$N(R_2)(R_3)$, —$C(O)N(R_2)(R_3)$, —CN, —$SC_{1-6}$alkyl, —NHC(O)NH$C_{1-6}$ alkyl, imine and substituted or unsubstituted triphenylphosphonium; and D) n is 0 or 1,
wherein when n is 0, either i) $R_{27}$ and $R_{28}$ represent H or ii) $R_{27}$ together with $R_{28}$ provide a second bond between $C^4$ and $C^5$;

or when n is 1, either i) $R_{24}$ and $R_{25}$ together form =O and $R_{27}$ and $R_{28}$ represent H or $R_{27}$ together with $R_{28}$ provide a second bond between $C^4$ and $C^5$ or $R_{26}$ and $R_{27}$ together form =O and $R_{28}$ represents H, or ii) $R_{24}$ and $R_{25}$ represent H and $R_{27}$ and $R_{28}$ represent H or $R_{27}$ together with $R_{28}$ provide a second bond between $C^4$ and $C^5$ or iii) $R_{24}$ represents H, $R_{25}$ together with $R_{27}$ provide a second bond between $C^3$ and $C^4$, $R_{26}$ represents —OH or a glycosidic functional group, $R_{28}$ represents —OH and X is —O—;

wherein said 3, 4, 5, 6, 7 or 8 membered saturated or unsaturated ring (Ring D) is optionally separated from $C^1$ or from the ring formed by $R_{20}$, $R_{21}$, $R_{22}$, and $R_{23}$ (Ring A) by —O—, —NH—, $C_1$-$C_6$ alkyl, —O—$C_1$-$C_6$ alkyl, —N—$C_1$-$C_6$ alkyl, $C_1$-$C_6$ alkenyl, or $C_2$-$C_6$ alkynyl;

wherein Ring A is a 5, 6 or 7 membered unsaturated carbocyclic ring, or a heterocycle wherein one or more available —CH— groups present in the 5, 6 or 7 membered unsaturated ring is optionally and independently replaced by —O—, —N—, —S—, —C(O)—, —S(O)$_p$—, or —N(R$_2$)—; wherein R$_2$ and R$_3$ each independently represent H or C$_{1-6}$ alkyl, and wherein p is 1 or 2;
and
wherein Ring D is a 3, 4, 5, 6, 7 or 8 membered saturated or unsaturated carbocycle, or a heterocycle wherein one or more available —CH— or —CH$_2$— groups present in the 3, 4, 5, 6, 7 or 8 membered saturated or unsaturated ring is optionally and independently replaced by —O—, —N—, —S—, —C(O)—, —S(O)$_p$—, or —N(R$_2$)—; wherein R$_2$ and R$_3$ each independently represent H or C$_{1-6}$ alkyl, and wherein p is 1 or 2;
and
wherein the total number of =O on Ring C is no greater than 2.

DETAILED DESCRIPTION OF THE INVENTION

The present invention provides compounds of Formula I as defined herein.

In some embodiments of the present invention,
R$_{20}$ represents H or a 3, 4, 5, 6, 7 or 8 membered saturated or unsaturated ring (Ring D);
R$_{21}$:
i) represents H;
ii) together with R$_{22}$ provides a second bond between C$^1$ and C$^2$; or
iii) when X is —NR$_1$— and R$_1$ is not H or C$_{1-6}$ alkyl, R$_{21}$ together with R$_1$ provides a second bond between C$^1$ and N;
R$_{22}$:
i) represents H;
ii) together with R$_{23}$ forms =O; or
iii) together with R$_2$, provides a second bond between C$^1$ and C$^2$;
R$_{23}$:
i) represents H or a 3, 4, 5, 6, 7 or 8 membered saturated or unsaturated ring (Ring D); or
ii) together with R$_{22}$ forms =O;
wherein at least one of R$_{20}$ and R$_{23}$ is a 3, 4, 5, 6, 7 or 8 membered saturated or unsaturated ring (Ring D).

Compounds or salts thereof according to this embodiment of the invention include compounds of the following Formula III:

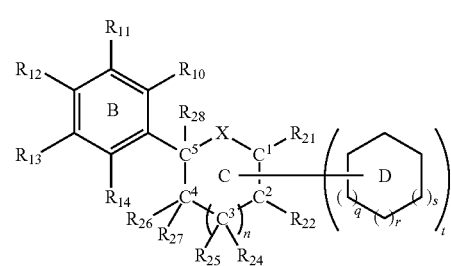

Formula III wherein p, q, r and s are each independently selected as follows:
q=0, 1 or 2
r=0, 1 or 2
s=0 or 1
t=1 or 2
wherein when t is 1, the remaining carbon atom (C$^1$ or C$^2$) to which Ring D is not attached has the corresponding R$_{20}$ or R$_{23}$ group attached and the corresponding R$_{20}$ or R$_{23}$ group is as defined above in relation to this embodiment of the invention (but is not Ring D). In other words, when t is 1, either R$_{20}$ (which is attached to C$^1$) represents Ring D and R$_{23}$ (which is attached to C$^2$) represents H or together with R$_{22}$ forms =O, or R$_{23}$ (which is attached to C$^2$) represents Ring D and R$_{20}$ (which is attached to C$^1$) represents H.

In other embodiments of the present invention,
R$_{20}$, R$_{21}$, R$_{22}$, and R$_{23}$ form part of a 5, 6 or 7 membered unsaturated ring including C$^1$ and C$^2$, which ring (Ring A) is substituted with at least one group;
said at least one group being a 3, 4, 5, 6, 7 or 8 membered saturated or unsaturated ring (Ring D); and
wherein the ring formed by R$_{20}$, R$_{21}$, R$_{22}$, and R$_{23}$ (Ring A) is optionally and independently further substituted with one or more groups independently selected from —OH and a 3, 4, 5, 6, 7 or 8 membered saturated or unsaturated ring (Ring D).

Compounds or salts thereof according to this embodiment of the invention include compounds of the following Formula II:

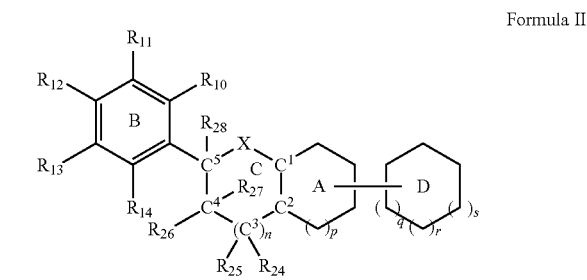

Formula II wherein p, q, r and s are each independently selected as follows:
p=0, 1 or 2
q=0, 1 or 2
r=0, 1 or 2
s=0 or 1
In some embodiments of the present invention, R$_{27}$ together with R$_{28}$ provide a second bond between C$^4$ and C$^5$.

In some embodiments of the present invention, X is O.

In some embodiments of the present invention n=0. In other embodiments of the present invention n=1.

In some embodiments of the present invention, R$_{24}$ and R$_{25}$ together form =O. In some embodiments, the total number of =O on Ring C is 1. In these embodiments, R$_{27}$ and R$_{28}$ represent H or R$_{27}$ together with R$_{28}$ provide a second bond between C$^4$ and C$^5$. In other embodiments, the total number of =O on Ring C is 2. In these embodiments, R$_{24}$ and R$_{25}$ together form =O and also R$_{26}$ and R$_{27}$ together form =O. In these embodiments, R$_{28}$ represents H.

In some embodiments of the present invention, R$_{12}$ and R$_{26}$ both represent OH. In some embodiments, R$_{12}$ represents =O. In some embodiments, R$_{26}$ and R$_{27}$ together form =O. In some embodiments, R$_{12}$ represents =O and R$_{26}$ and R$_{27}$ together form =O. In some embodiments, R$_{10}$ represents =O. In some embodiments, R$_{11}$ represents =O. In some embodiments, R$_{13}$ represents =O. In some embodiments, R$_{10}$ represents =O and R$_{26}$ and R$_{27}$ together form =O. In some embodiments, R$_{10}$ represents =O and R$_{13}$ represents =O. In some embodiments, R$_{11}$ represents =O and R$_{12}$ represents =O.

In some embodiments therefore, the compounds of the invention include ortho or para quinones on the B-ring, or extended quinones between the B-ring and C-ring of the molecule.

In some embodiments of the present invention, $R_{11}$ and $R_{13}$ both represent OH. In some embodiments, $R_{11}$ and $R_{12}$ both represent OH. In some embodiments, $R_{11}$, $R_{12}$ and $R_{13}$ all represent OH.

In some embodiments of the present invention, $R_{11}$ and/or $R_{13}$ represent $C_{1-6}$ alkoxy-, for example methoxy, ethoxy, propoxy, butoxy or pentoxy, typically methoxy. In some embodiments, $R_{11}$ and $R_{13}$ both represent methoxy. In some embodiments, $R_{11}$ represents methoxy and $R_{13}$ represents H.

In some or all embodiments of the present invention, $R_{12}$ and $R_{26}$ may both represent OH; or one but not both of $R_{12}$ and $R_{26}$ may represent a glycosidic functional group, for example $R_{12}$ may be OH when $R_{26}$ is a glycosidic functional group or vice versa. In some embodiments of the present invention, one or both of $R_{11}$ and $R_{13}$ may represent OH; and/or $R_{10}$ and $R_{14}$ each independently represent H, OH or $C_{1-6}$-alkoxy-. An example of such a compound, wherein X=O and $R_{27}$ together with $R_{28}$ provides a second bond between $C^4$ and $C^5$ is the compound of Formula IV or a salt thereof:

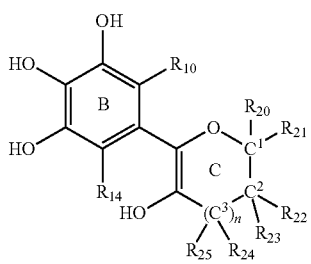

Formula IV wherein:
A) $R_{10}$ and $R_{14}$ each independently represent H, —OH, nitro, halogen, amino, amido, cyano, carboxyl, sulphonyl, a glycosidic functional group substituent, $C_{1-6}$ alkoxy-, hydroxy $C_{1-6}$ alkyl-, $C_{1-6}$ alkoxy-$C_{1-6}$ alkyl-, or a saturated or unsaturated $C_{1-6}$ hydrocarbon chain which may be substituted with one or more of nitro, halogen, amino, amido, cyano, carboxyl, sulphonyl, hydroxyl, ketone or aldehyde; and wherein Ring B comprises no more than one glycosidic functional group substituent;

B) either a):
  $R_{20}$ represents H or a 3, 4, 5, 6, 7 or 8 membered saturated or unsaturated ring (Ring D);
  $R_{21}$:
  i) represents H; or
  ii) together with $R_{22}$ provides a second bond between $C^1$ and $C^2$;
  $R_{22}$:
  i) represents H;
  ii) together with $R_{23}$ forms =O; or
  iii) together with $R_{2}$, provides a second bond between $C^1$ and $C^2$; and
  $R_{23}$:
  i) represents H or a 3, 4, 5, 6, 7 or 8 membered saturated or unsaturated ring (Ring D); or
  ii) together with $R_{22}$ forms =O;
wherein at least one of $R_{20}$ and $R_{23}$ is a 3, 4, 5, 6, 7 or 8 membered saturated or unsaturated ring (Ring D);
or b)
  $R_{20}$, $R_{21}$, $R_{22}$ and $R_{23}$ form part of a 5, 6 or 7 membered unsaturated ring including $C^1$ and $C^2$ (Ring A), which ring is substituted with at least one group, said at least one group being a 3, 4, 5, 6, 7 or 8 membered saturated or unsaturated ring (Ring D);

wherein the ring formed by $R_{20}$, $R_{21}$, $R_{22}$, and $R_{23}$ (Ring A) is optionally and independently further substituted with one or more groups independently selected from —OH and a 3, 4, 5, 6, 7 or 8 membered saturated or unsaturated ring (Ring D);

wherein the ring formed by $R_{20}$, $R_{21}$, $R_{22}$, and $R_{23}$ (Ring A) and the 3, 4, 5, 6, 7 or 8 membered saturated or unsaturated ring (Ring D) are optionally and independently further substituted with one or more groups selected from an O—, S—, or N-containing functional group, for example, nitro, hydroxyl, carboxyl, ketone, amino, or thiol, or benzyl, phenyl, unsaturated 5, 6, 7 or 8 membered ring, cycloalkyl, cycloalkenyl, cycloalkynyl, amido, cyano, sulphonyl, aldehyde, nitrone, $C_2$-$C_6$ alkenyl, $C_2$-$C_6$ alkynyl, —NH$_2$, —F, $C_{1-6}$ alkoxy, hydroxy-$C_{1-6}$ alkyl, —CO$_2$H, —CO$_2$C$_{1-6}$alkyl, —S(O)$_2$C$_{1-6}$alkyl, —S(O)$_2$-phenyl, —NO$_2$, —OH, —N(R$_2$)(R$_3$), —C(O)N(R$_2$)(R$_3$), —CN, —SC$_{1-6}$alkyl, —NHC(O)NHC$_{1-6}$ alkyl, imine and substituted or unsubstituted triphenylphosphonium; and C) n is 0 or 1, wherein when n is 1, either i) $R_{24}$ and $R_{25}$ together form =O, or ii) $R_{24}$ and $R_{25}$ represent H;

wherein said 3, 4, 5, 6, 7 or 8 membered saturated or unsaturated ring (Ring D) is optionally separated from $C^1$ or from the ring formed by $R_{20}$, $R_{21}$, $R_{22}$, and $R_{23}$ (Ring A) by —O—, —NH—, $C_1$-$C_6$ alkyl, $C_1$-$C_6$ alkenyl, or $C_2$-$C_6$ alkynyl;

wherein Ring A is a 5, 6 or 7 membered unsaturated carbocyclic ring, or a heterocycle wherein one or more available —CH— groups present in the 5, 6 or 7 membered unsaturated ring is optionally and independently replaced by —O—, —N—, —S—, —C(O)—, —S(O)$_p$—, or —N(R$_2$)—; wherein $R_2$ and $R_3$ each independently represent H or $C_{1-6}$ alkyl, and wherein p is 1 or 2;

wherein Ring D is a 3, 4, 5, 6, 7 or 8 membered saturated or unsaturated carbocycle, or a heterocycle wherein one or more available —CH— or —CH$_2$— groups present in the 3, 4, 5, 6, 7 or 8 membered saturated or unsaturated ring is optionally and independently replaced by —O—, —N—, —S—, —C(O)—, —S(O)$_p$—, or —N(R$_2$)—; wherein $R_2$ and $R_3$ each independently represent H or $C_{1-6}$ alkyl, and wherein p is 1 or 2;
and
wherein the total number of =O on ring C is no greater than 2.

In one embodiment of the invention, the compound is a compound of Formula IV or a salt thereof, wherein:
A) $R_{10}$ and $R_{14}$ each represent H;
B) either a):
  $R_{20}$ represents a 3, 4, 5, 6, 7 or 8 membered saturated or unsaturated ring (Ring D);
  $R_{21}$ together with $R_{22}$ provides a second bond between $C^1$ and $C^2$; and
  $R_{23}$ represents H;
or b):
  $R_{20}$, $R_{21}$, $R_{22}$ and $R_{23}$ form part of a 5, 6 or 7 membered unsaturated ring including $C^1$ and $C^2$ (Ring A), which ring is substituted with at least one group, said at least one group being a 3, 4, 5, 6, 7 or 8 membered saturated or unsaturated ring (Ring D); and
C) $R_{24}$ and $R_{25}$ together form =O.

A further example of a compound of Formula I, but wherein X=O, n=1, $R_{11}$, $R_{12}$ and $R_{13}$ each represent OH, $R_{24}$ together with $R_{25}$ forms =O and $R_{27}$ together with $R_{28}$ provides a second bond between $C^4$ and $C^5$, is the compound of Formula V or salt thereof:

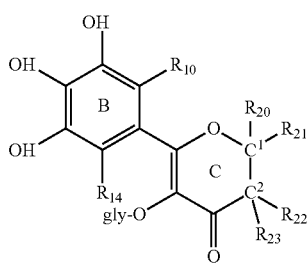

Formula V wherein:

A) $R_{10}$ and $R_{14}$ each independently represent H, —OH, nitro, halogen, amino, amido, cyano, carboxyl, sulphonyl, a glycosidic functional group substituent, $C_{1-6}$ alkoxy-, hydroxy $C_{1-6}$ alkyl-, $C_{1-6}$ alkoxy-$C_{1-6}$ alkyl-, or a saturated or unsaturated $C_{1-6}$ hydrocarbon chain which may be substituted with one or more of nitro, halogen, amino, amido, cyano, carboxyl, sulphonyl, hydroxyl, ketone or aldehyde; and wherein ring B comprises no more than one glycosidic functional group substituent; and O-gly represents a glycosidic functional group substituent;

B) either a):
  $R_{20}$ represents H or a 3, 4, 5, 6, 7 or 8 membered saturated or unsaturated ring (Ring D);
  $R_{21}$:
  i) represents H; or
  ii) together with $R_{22}$ provides a second bond between $C^1$ and $C^2$;
  $R_{22}$:
  i) represents H; or
  ii) together with $R_2$, provides a second bond between $C^1$ and $C^2$; and
  $R_{23}$ represents H or a 3, 4, 5, 6, 7 or 8 membered saturated or unsaturated ring (Ring D);
  wherein at least one of $R_{20}$ and $R_{23}$ is a 3, 4, 5, 6, 7 or 8 membered saturated or unsaturated ring (Ring D);
or b)
  $R_{20}$, $R_{21}$, $R_{22}$ and $R_{23}$ form part of a 5, 6 or 7 membered unsaturated ring including $C^1$ and $C^2$ (Ring A), which ring is substituted with at least one group, said at least one group being a 3, 4, 5, 6, 7 or 8 membered saturated or unsaturated ring (Ring D);
  wherein the ring formed by $R_{20}$, $R_{21}$, $R_{22}$, and $R_{23}$ (Ring A) is optionally and independently further substituted with one or more groups independently selected from —OH and a 3, 4, 5, 6, 7 or 8 membered saturated or unsaturated ring (Ring D);
wherein the ring formed by $R_{20}$, $R_{21}$, $R_{22}$, and $R_{23}$ (Ring A) and the 3, 4, 5, 6, 7 or 8 membered saturated or unsaturated ring (Ring D) are optionally and independently further substituted with one or more groups selected from an O—, S—, or N-containing functional group, for example, nitro, hydroxyl, carboxyl, ketone, amino, or thiol, or benzyl, phenyl, unsaturated 5, 6, 7 or 8 membered ring, cycloalkyl, cycloalkenyl, cycloalkynyl, amido, cyano, sulphonyl, aldehyde, nitrone, $C_2$-$C_6$ alkenyl, $C_2$-$C_6$ alkynyl, —NH$_2$, —F, $C_{1-6}$ alkoxy, hydroxy-$C_{1-6}$ alkyl, —CO$_2$H, —CO$_2$C$_{1-6}$alkyl, —S(O)$_2$C$_{1-6}$alkyl, —S(O)$_2$-phenyl, —NO$_2$, —OH, —N(R$_2$)(R$_3$), —C(O)N(R$_2$)(R$_3$), —CN, —SC$_{1-6}$alkyl, —NHC(O)NHC$_{1-6}$ alkyl, imine and substituted or unsubstituted triphenylphosphonium.

In one embodiment of the present invention, $R_{20}$ represents H or a 3, 4, 5, 6, 7 or 8 membered saturated or unsaturated ring (Ring D); $R_{21}$: i) represents H; ii) together with $R_{22}$ provides a second bond between $C^1$ and $C^2$; or iii) when X is —NR$_1$— and R$_1$ is not H or C$_{1-6}$ alkyl, $R_{21}$ together with R$_1$ provides a second bond between $C^1$ and N; $R_{22}$: i) represents H; ii) together with $R_{23}$ forms =O; or iii) together with $R_2$, provides a second bond between $C^1$ and $C^2$; $R_{23}$: i) represents H or a 3, 4, 5, 6, 7 or 8 membered saturated or unsaturated ring (Ring D); or ii) together with $R_{22}$ forms =O; wherein at least one of $R_{20}$ and $R_{23}$ is a 3, 4, 5, 6, 7 or 8 membered saturated or unsaturated ring (Ring D). Compounds of this embodiment of the invention are shown in Formula III above.

In one embodiment of the present invention, Ring C is substituted in the $R_{20}$ or $R_{23}$ position with Ring D. Typically, Ring C is substituted in the $R_{20}$ position with Ring D. In another embodiment of the present invention, Ring C is substituted in the $R_{20}$ and $R_{23}$ position with Ring D. In this embodiment, Ring C is substituted with 2 occurrences of Ring D.

In one embodiment of the present invention, $R_{20}$, $R_{21}$, $R_{22}$, and $R_{23}$ form part of a 5, 6 or 7 membered unsaturated ring including $C^1$ and $C^2$, which ring (Ring A) is substituted with at least one group, said at least one group being a 3, 4, 5, 6, 7 or 8 membered saturated or unsaturated ring (Ring D); and wherein the 3, 4, 5, 6, 7 or 8 membered saturated or unsaturated ring (Ring D) is at the meta, para or ortho position relative to $C^1$. Compounds of this embodiment of the invention are shown in Formula II above.

Typically, $R_{20}$, $R_{21}$, $R_{22}$, and $R_{23}$ form part of a 6 membered unsaturated ring including $C^1$ and $C^2$. Typically, the 3, 4, 5, 6, 7 or 8 membered saturated or unsaturated ring (Ring D) is at the meta position relative to $C^1$. In some embodiments, the 3, 4, 5, 6, 7 or 8 membered saturated or unsaturated ring (Ring D) is not at the ortho position relative to $C^1$. In some embodiments, the 3, 4, 5, 6, 7 or 8 membered saturated or unsaturated ring (Ring D) is not at the para position relative to $C^1$.

By "the ortho position relative to $C^1$" is meant the carbon next to the $C^1$ on the ring (Ring A). By "the meta position relative to $C^1$" is meant the carbon next to the ortho position remote from $C^1$. By "the para position relative to $C^1$" is meant the carbon next to the meta position remote from $C^1$.

It will be appreciated by those skilled in the art that in the case of 5 membered rings, the para position may also be defined as the meta position. When Ring A is a 5 membered ring, the ring can be substituted with Ring D at the first, second or third carbon, when counting carbon atoms clockwise from $C^1$ in the formulae as depicted herein.

Similarly, when Ring A is a 7 membered ring, the ring can be substituted with Ring D at the first, second, third, fourth or fifth carbon, when counting carbon atoms clockwise from $C^1$.

In one embodiment of the present invention, the ring formed by $R_{20}$, $R_{21}$, $R_{22}$, and $R_{23}$ (Ring A) is a 5, 6 or 7 membered unsaturated carbocyclic ring.

Alternatively, the ring formed by $R_{20}$, $R_{21}$, $R_{22}$, and $R_{23}$ (Ring A) is a 5, 6 or 7 membered unsaturated heterocycle, having 1, 2, or 3 heteroatoms, independently selected from O, N or S.

In the present invention, Ring A can be, for example, 1H-azepine, oxepine, thiepine, pyridine, pyridazine, pyrimidine, pyrazine, 1,3,5-triazine, pyrrole, furan, thiophene, pyrazole, imidazole, oxazole, isoxazole, furazan, 1,3,4-thiadiazole, thiazole, isothiazole, 1,2,3-triazole, 1,2,4-triazole and 1,2,3-oxadiazole.

In one embodiment of the present invention, Ring A is substituted with 1 or 2 occurrences of —OH.

In one embodiment of the present invention, Ring D is a 3, 4, 5, 6, 7 or 8 membered saturated or unsaturated carbocycle.

In another embodiment of the present invention, Ring D is a 5, 6, 7, or 8 membered saturated or unsaturated heterocyclic ring, having 1, 2, or 3 heteroatoms, independently selected from O, N or S. In this embodiment of the present invention, Ring D is typically a 5, 6, or 7 membered heterocyclic ring, having 1, 2, or 3 heteroatoms, independently selected from O, N or S. Typically, Ring D is a 5 or 6 membered heterocyclic ring, having 1, 2, or 3 heteroatoms, independently selected from O, N or S. Typically, Ring D is a 6 membered heterocyclic ring, having 1 or 2 heteratoms, independently selected from O and N. When Ring D is a 6 membered heterocyclic ring having 1 heteratom, the heteroatom is typically N. When Ring D is a 6 membered heterocyclic ring having 2 heteratoms, the heteroatoms are typically one each of O and N.

In the present invention, Ring D can be, for example, pyrrolidine, tetrahydrofuran, tetrahydrothiophene, pyrazolidine, imidazolidine, thiazolidine, isoxazolidine, piperidine, piperazine, morpholine, 1,4-dioxane, thiomorpholine, 1,4-oxathiane, 1,4-dithiane, 1,3,5-thioxane, 1,3,5-trithiane, 1H-azepine, oxepine, thiepine, pyridine, pyridazine, pyrimidine, pyrazine, 1,3,5-triazine, pyrrole, furan, thiophene, pyrazole, imidazole, oxazole, isoxazole, furazan, 1,3,4-thiadiazole, thiazole, isothiazole, 1,2,3-triazole, 1,2,4-triazole and 1,2,3-oxadiazole.

In one embodiment of the present invention, Ring D is a 3, 4, 5, 6, 7 or 8 membered saturated ring.

In some embodiments, Ring D is a sugar group, for example deoxyglucose. In some embodiments, the sugar group is not glucose or rhamnose.

In some embodiment of the present invention, Ring D is substituted with 1 or 2 occurrences of —NH$_2$. In some embodiments of the present invention, Ring D is substituted with 1 or 2 occurrences of —F. In some embodiments of the present invention, Ring D is substituted with 1 or 2 occurrences of —OH. In some embodiments of the present invention, Ring D is substituted with 1 or 2 methoxy groups. In some embodiments, Ring D is substituted with 2 occurrences of —OH and a methoxy group.

In one embodiment of the present invention, Ring D is separated from $C^1$ (when no Ring A is present) or from Ring A by —O—, —NH—, a $C_1$-$C_6$ alkyl, for example a $C_1$ alkyl, a $C_2$ alkyl, a $C_3$ alkyl or a $C_4$ alkyl, —O—$C_1$-$C_6$ alkyl, for example —O—CH$_2$— or —N—$C_1$-$C_6$ alkyl, for example —N—CH$_2$—. In other embodiments, Ring D is directly attached to $C^1$ (when no Ring A is present) or Ring A.

Examples of compounds and salts thereof falling within the scope of the present invention include compounds of the following Formula VI:

Formula VI

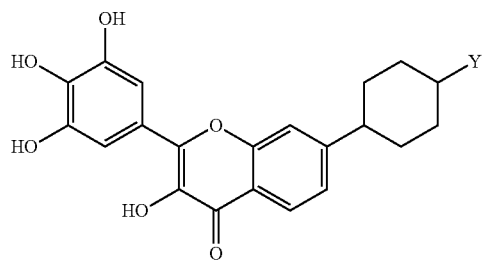

wherein Y is NH$_2$ or F.

Compounds falling within the scope of Formula VI are the following:

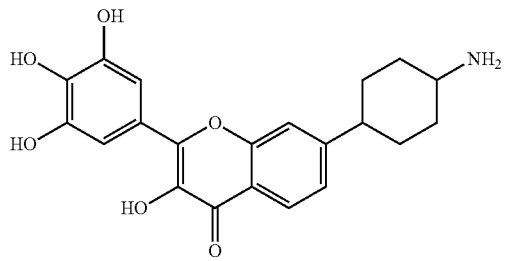

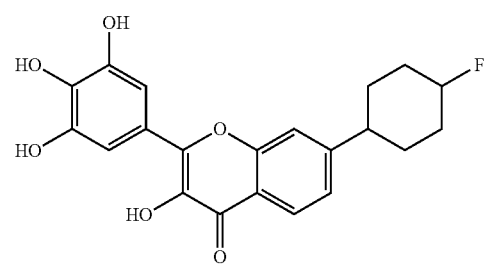

Examples of specific compounds or salts thereof within the scope of the present invention include the following compounds falling within the scope of Formula II:

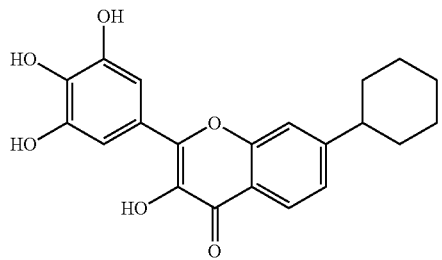

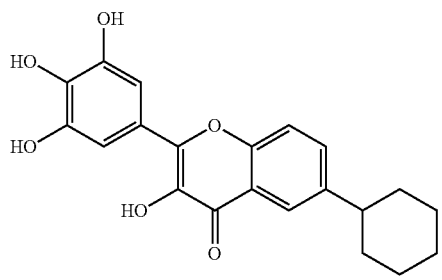

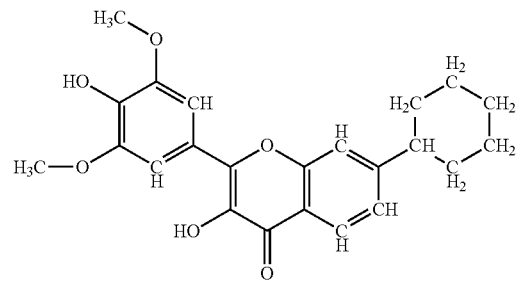

-continued
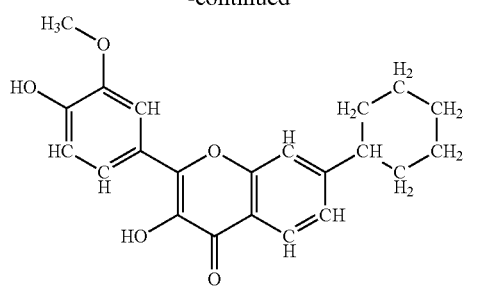
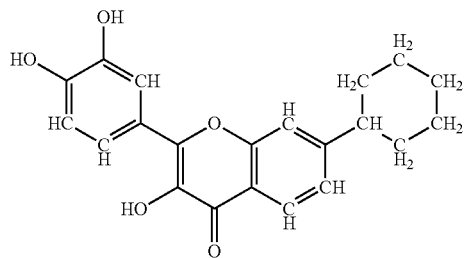
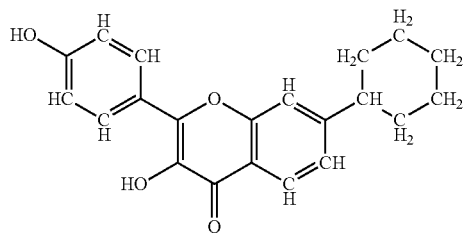
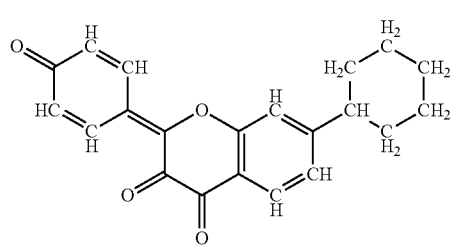
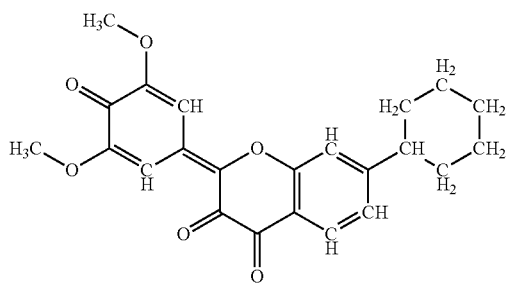
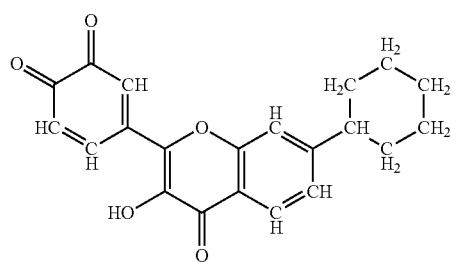
-continued
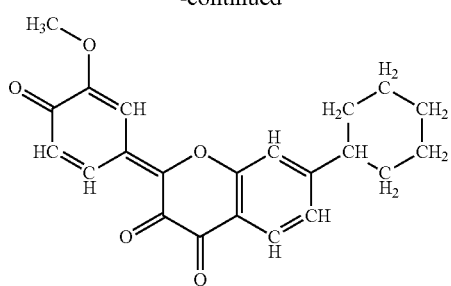
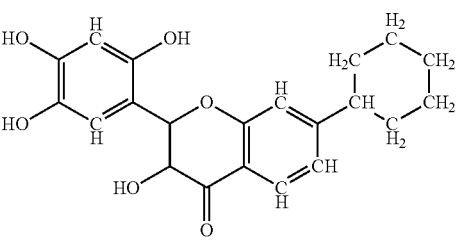
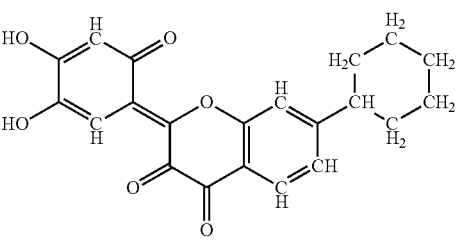
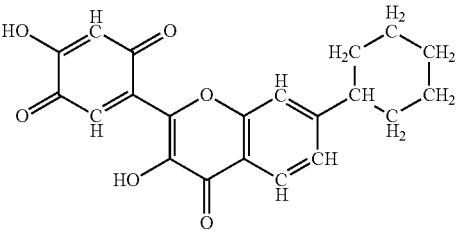
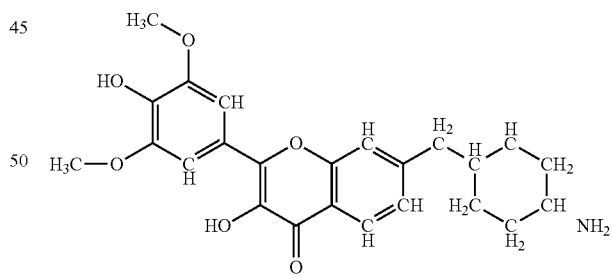
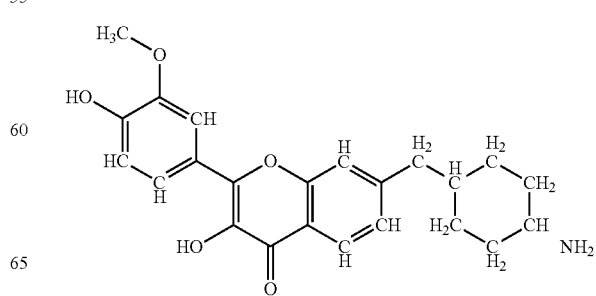

-continued
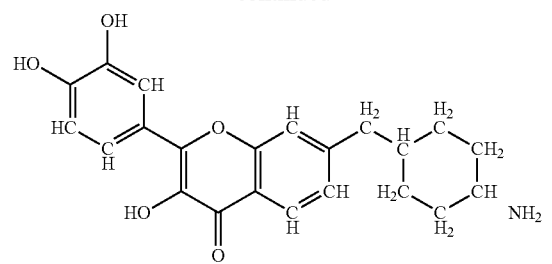
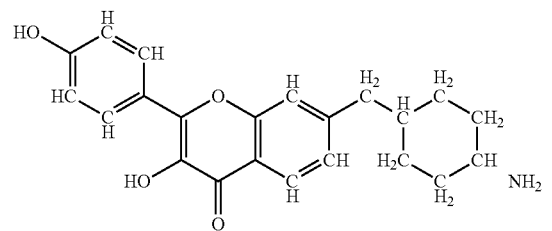
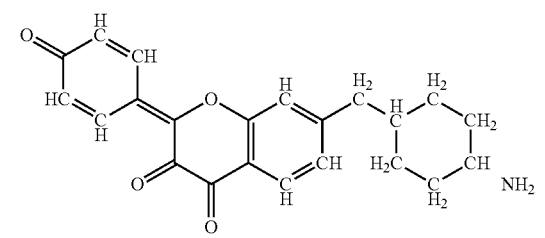
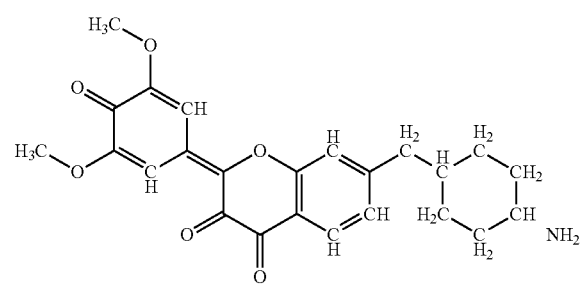
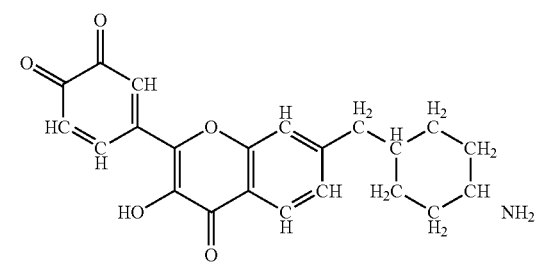
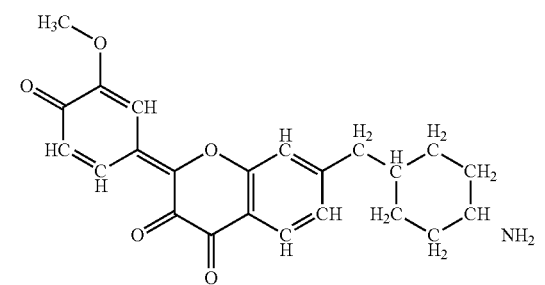
-continued
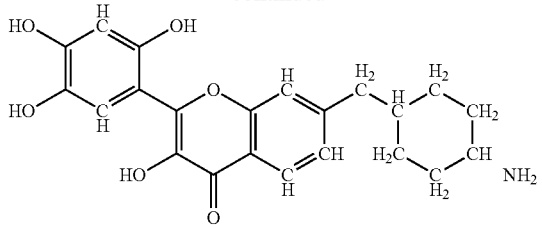
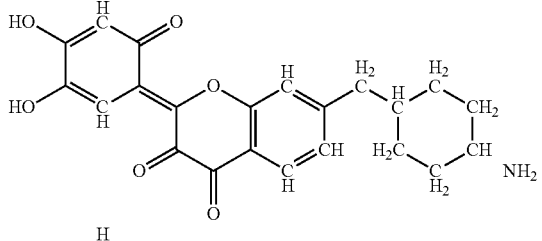
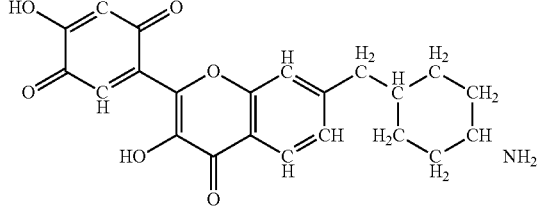
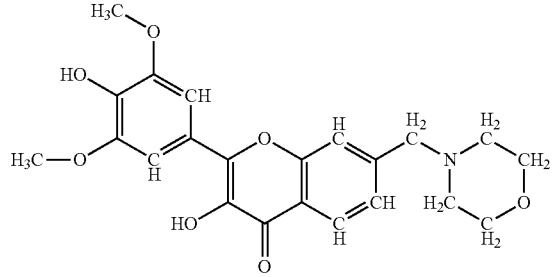
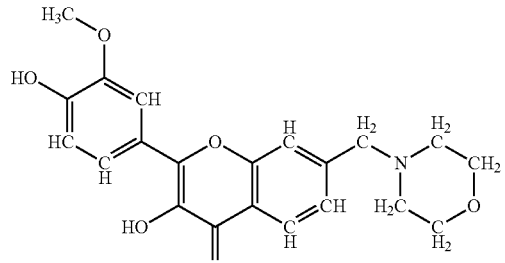
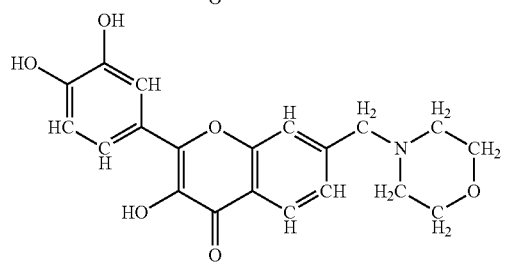
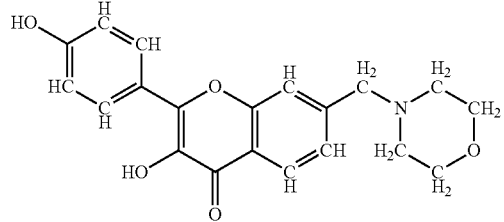

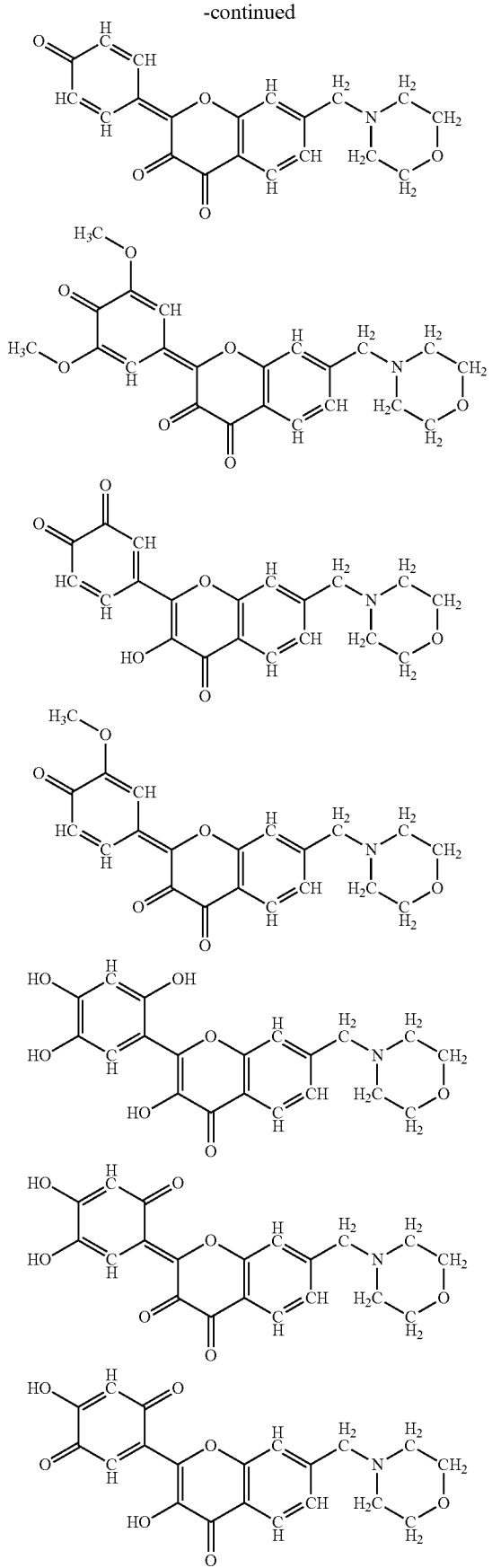
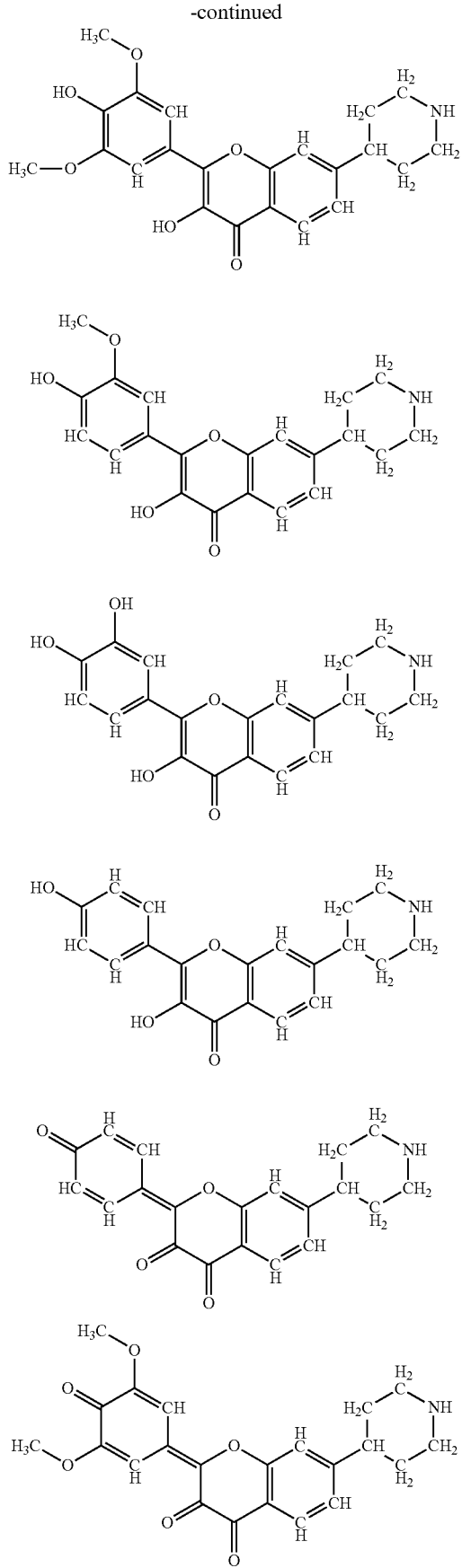

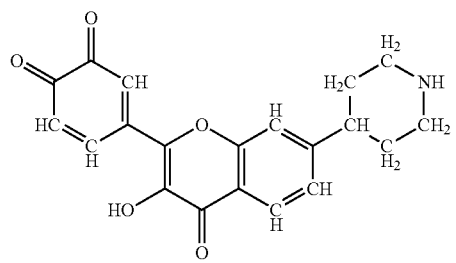
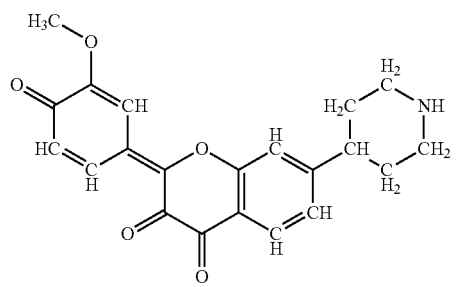
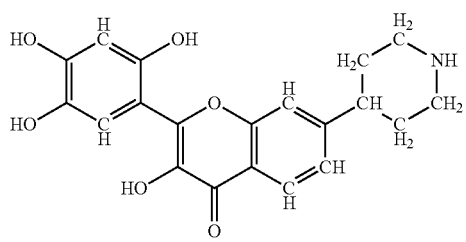
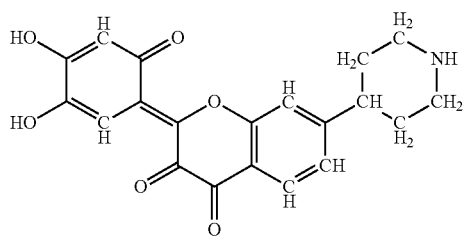
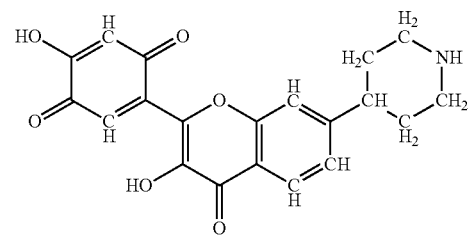
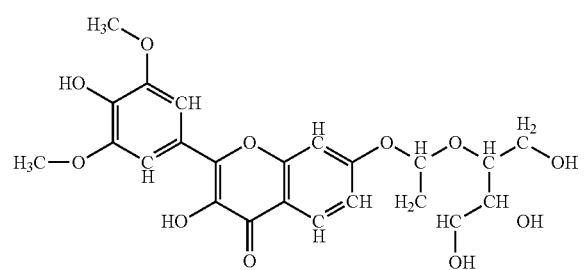
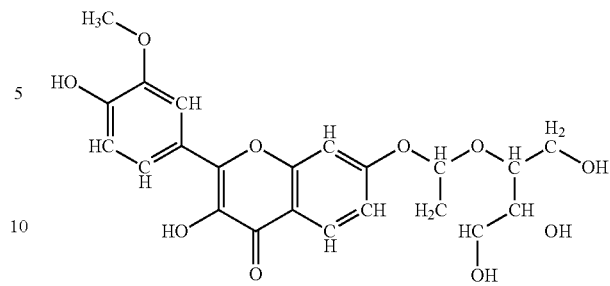
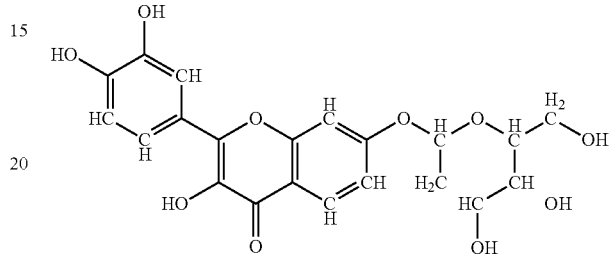
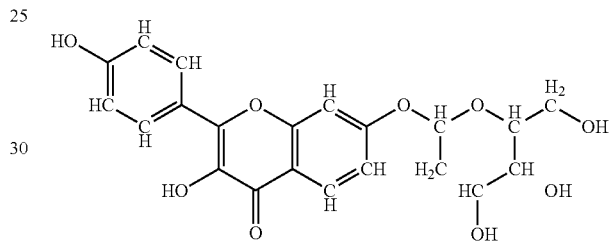
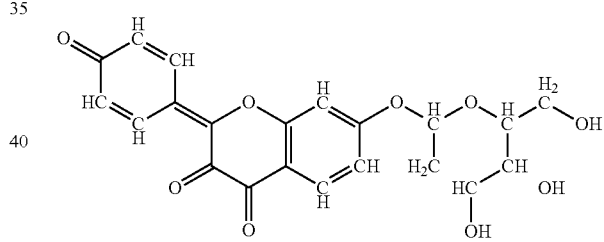
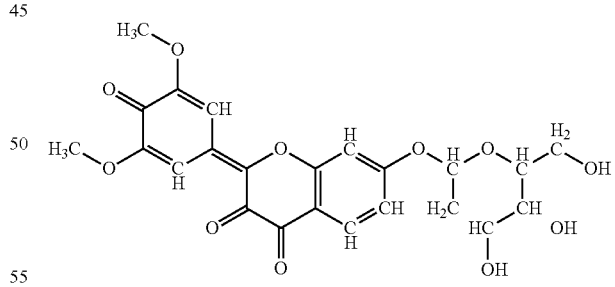
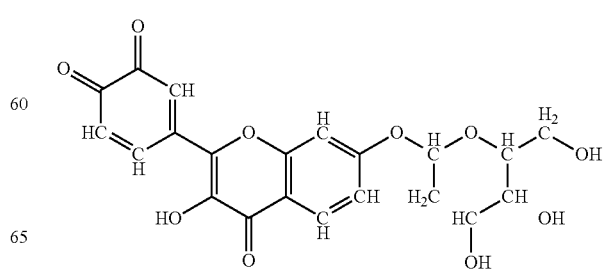

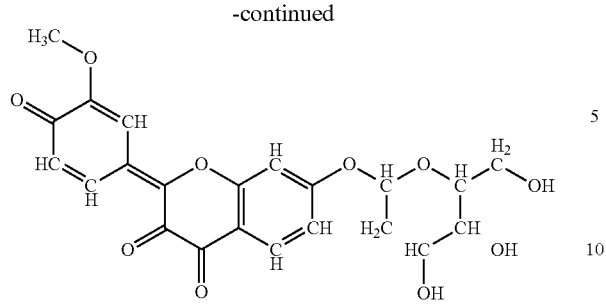
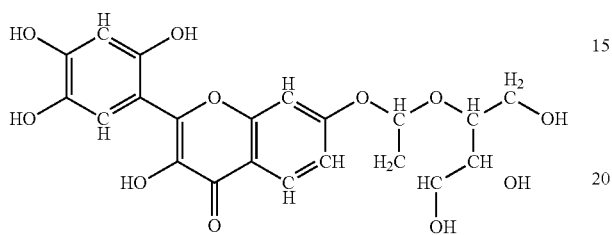
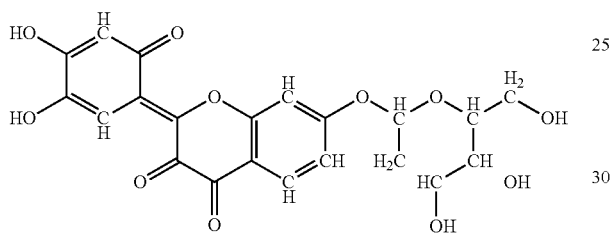
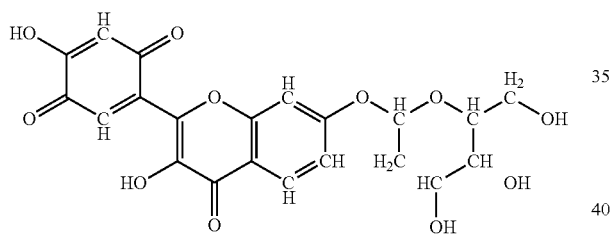
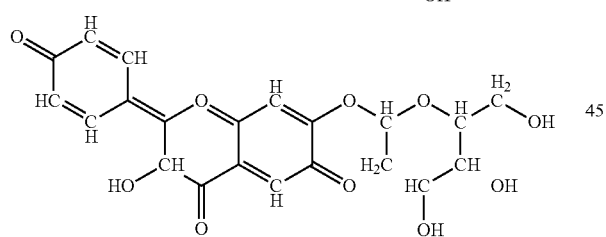
Further examples of specific compounds or salts thereof within the scope of the present invention include the following compounds falling within the scope of Formula III:
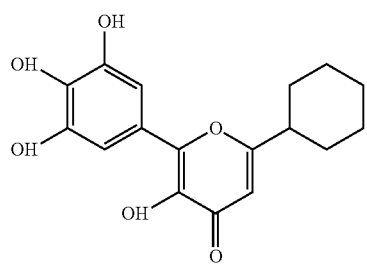
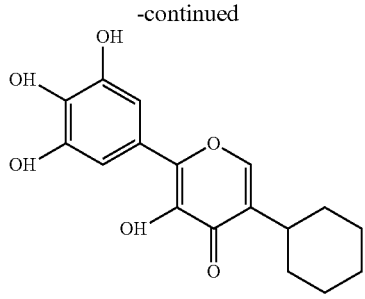
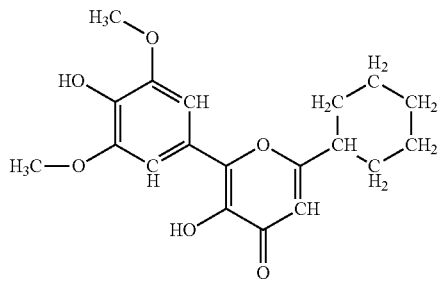
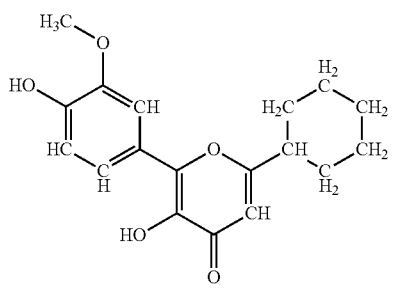
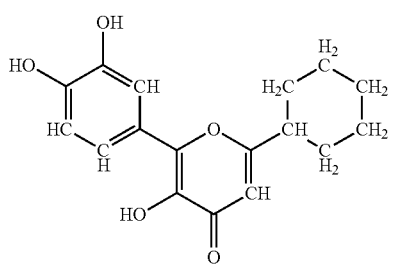
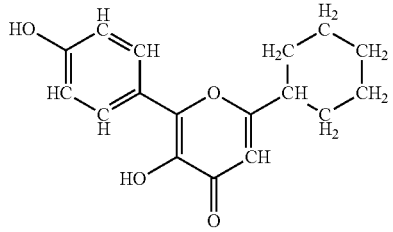
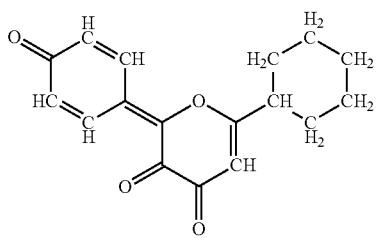

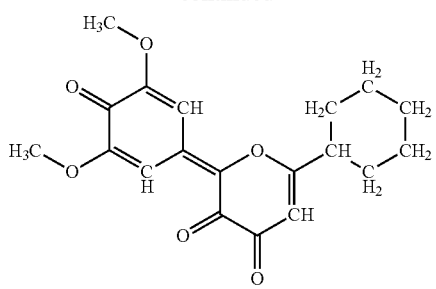
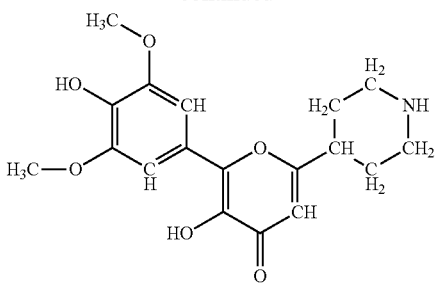
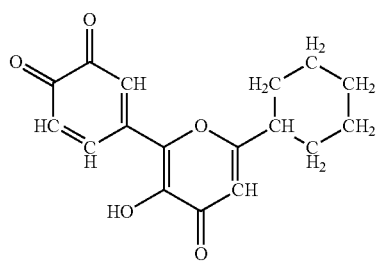
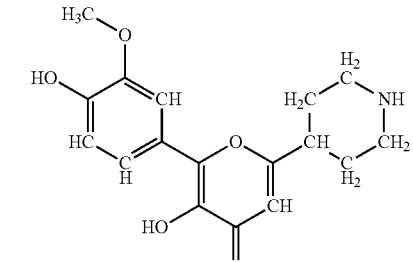
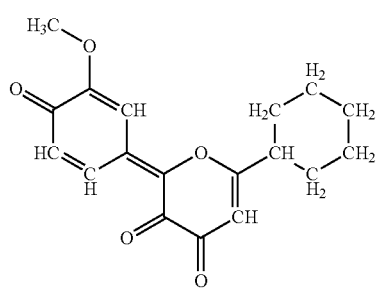
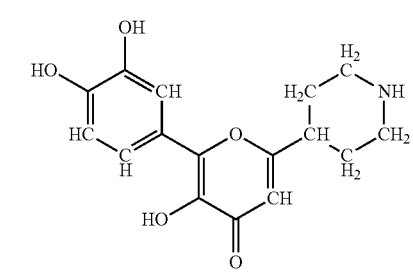
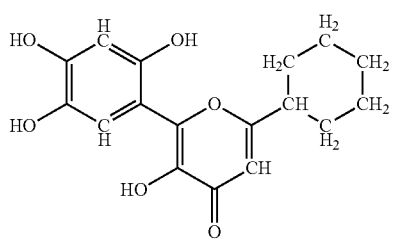
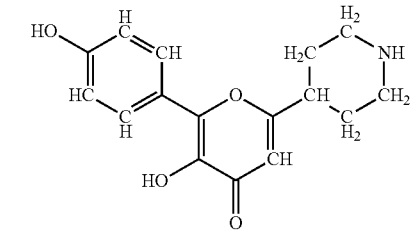
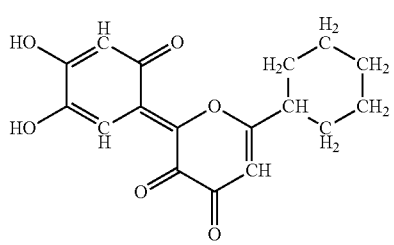
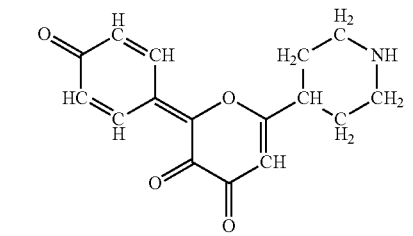
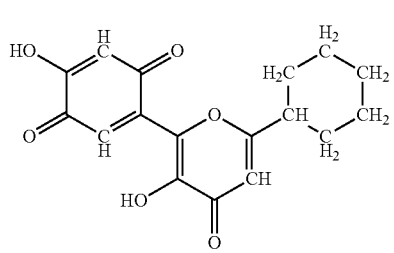
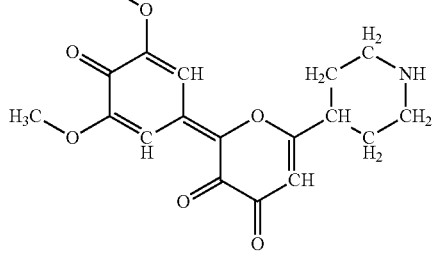

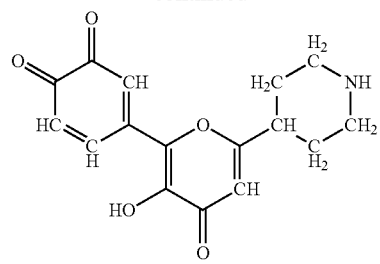
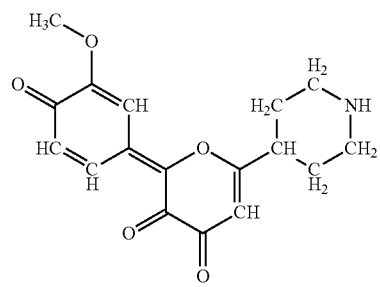
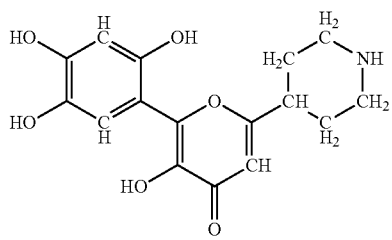
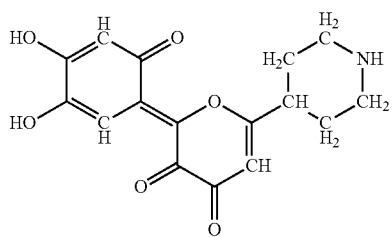
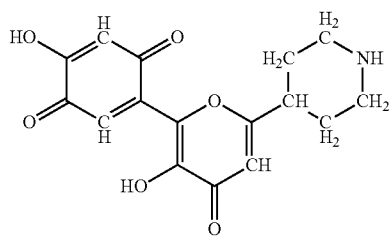
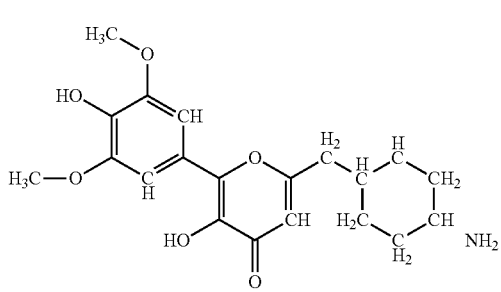
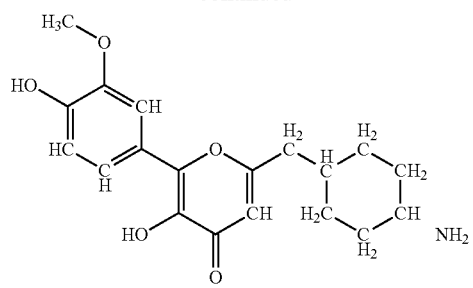
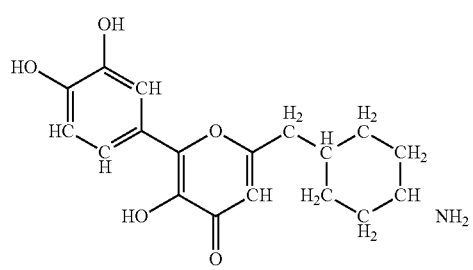
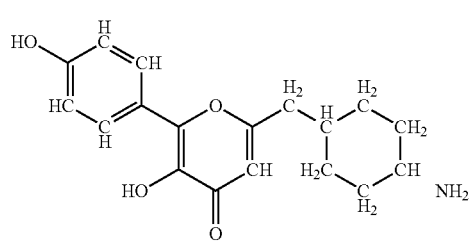
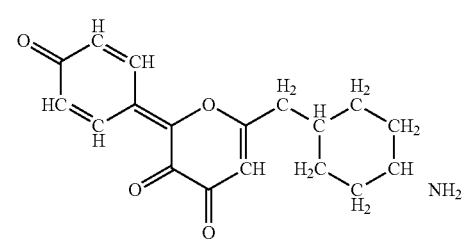
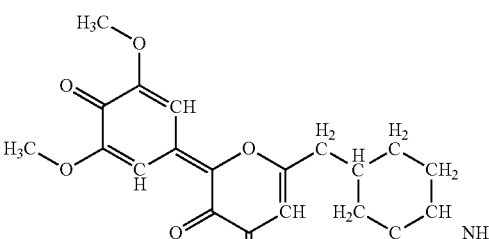
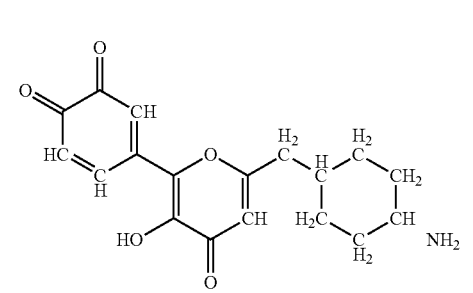

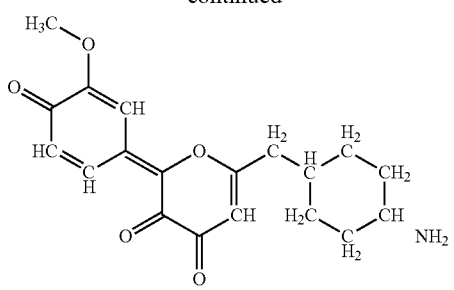
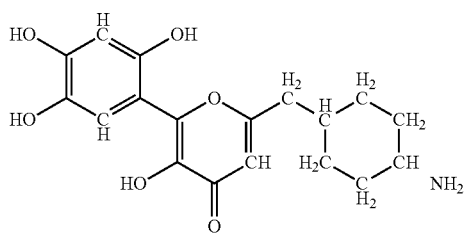
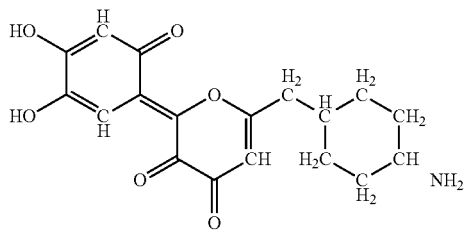
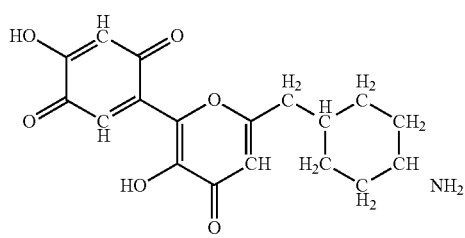
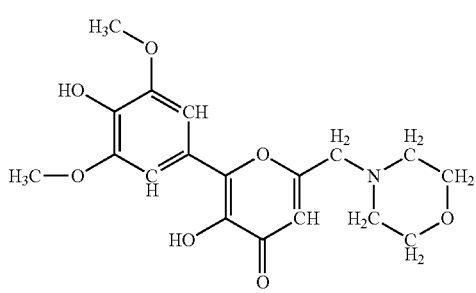
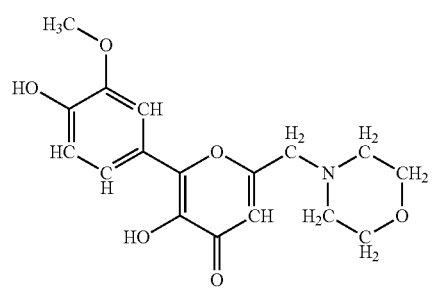
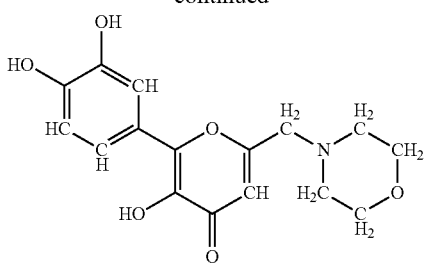
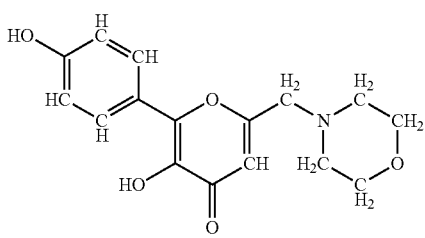
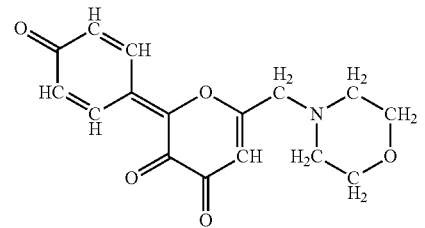
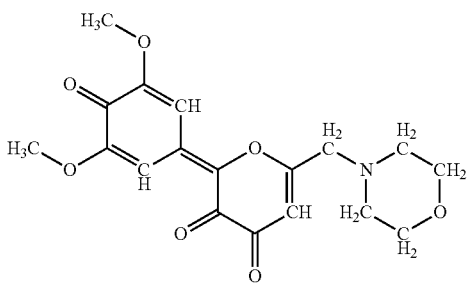
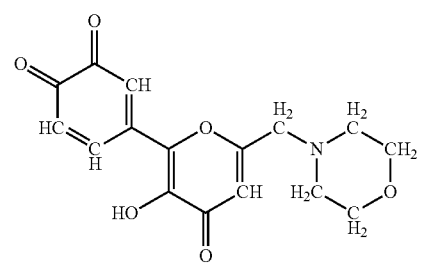
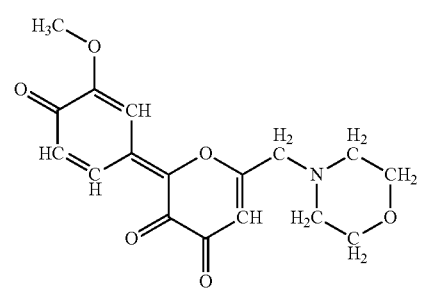

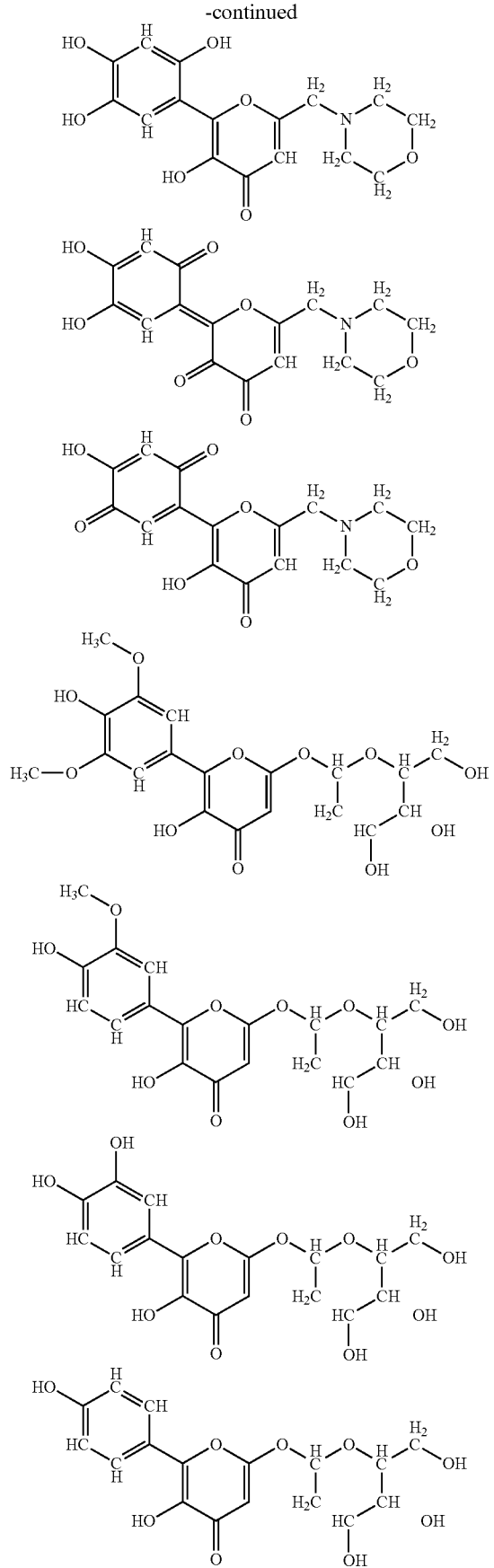
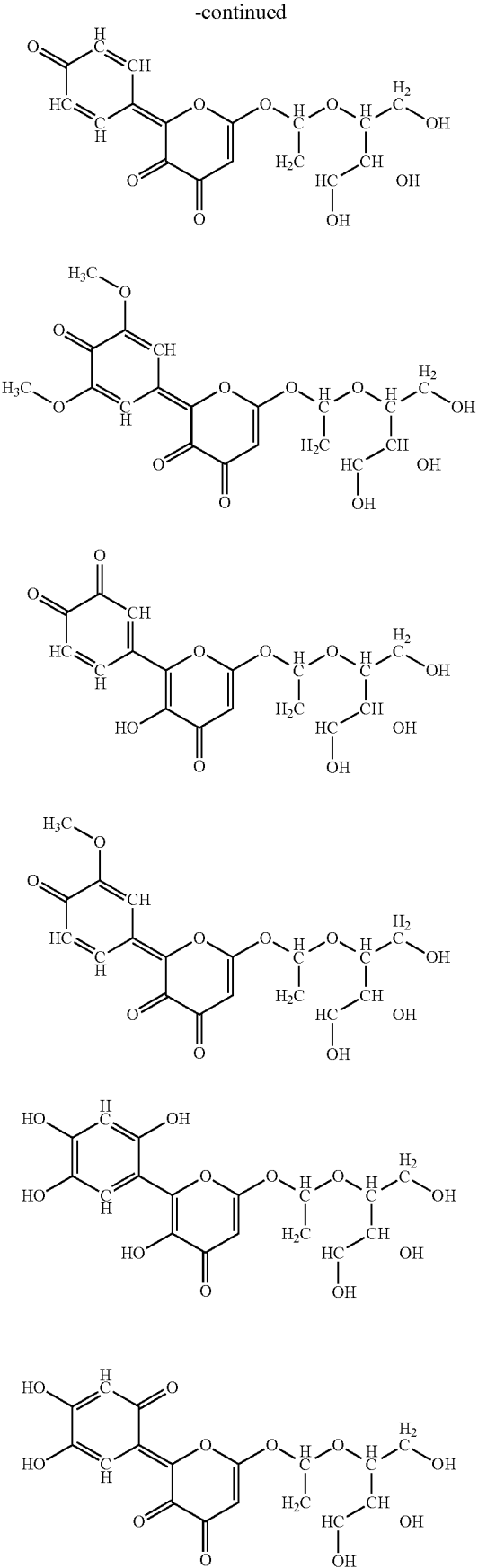

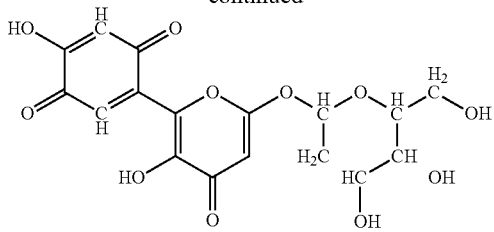

Without being bound by theory, the compounds of the present invention differ from those of the prior art, for example those disclosed in WO 2004/007475 and WO 2009/047568 in that hydrocarbon chains are replaced by a ring system. The idea behind this is to reduce the number of rotatable bonds in the antioxidant molecules which should improve blood-brain barrier permeability. At the same time a significant lipophilic presence is retained at this site on the molecule.

For the quinone compounds of the invention, reductase enzymes will reduce quinones in vivo to the active antioxidant form. Consequently, administration of the quinone should enhance antioxidant activity, but be preferable in terms of drug attributes.

As used herein, the following definitions shall apply unless otherwise indicated.

The phrase "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other.

The terms "alkyl", "alkoxy", "hydroxyalkyl", and "alkoxyalkyl", used alone or as part of a larger moiety includes both straight and branched chains containing one to twelve carbon atoms. The terms "alkenyl" and "alkynyl" used alone or as part of a larger moiety include both straight and branched chains containing two to six carbon atoms. The term "cycloalkyl" used alone or as part of a larger moiety includes cyclic $C_3$-$C_{12}$ hydrocarbons which are completely saturated or which contain one or more units of unsaturation, but which are not aromatic.

The term "halogen" means F, Cl, Br, or I.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or NR⁺ (as in N-substituted pyrrolidinyl).

The terms "carbocycle" or "carbocyclic" as used herein means an aliphatic ring system having three to fourteen members. The terms "carbocycle" or "carbocyclic" whether saturated or partially unsaturated, also refers to rings that are optionally substituted. The terms "carbocycle" or "carbocyclic" also include aliphatic rings that are fused to one or more aromatic or nonaromatic rings, such as in a decahydronaphthyl or tetrahydronaphthyl, where the radical or point of attachment is on the aliphatic ring.

The term "heterocycle" or "heterocyclic" as used herein includes non-aromatic ring systems having three to eight members, preferably five to seven, in which one or more ring carbons, preferably one to four, are each replaced by a heteroatom such as N, O, or S. Examples of heterocyclic rings include 3-1H-benzimidazol-2-one, (1-substituted)-2-oxobenzimidazol-3-yl, 2-tetrahydrofuranyl, 3-tetrahydrofuranyl, 2-tetrahydropyranyl, 3-tetrahydropyranyl, 4-tetrahydropyranyl, [1,3]-dioxalanyl, [1,3]-dithiolanyl, [1,3]-dioxanyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzopyrrolidinyl, benzopiperidinyl, benzoxolanyl, benzothiolanyl, and benzothianyl. Also included within the scope of the term "heterocyclic", as it is used herein, is a group in which a non-aromatic heteroatom-containing ring is fused to one or more aromatic or non-aromatic rings, such as in an indolinyl, chromanyl, phenanthridinyl, or tetrahydroquinolinyl, where the radical or point of attachment is on the non-aromatic heteroatom-containing ring. The term "heterocycle" or "heterocyclic" whether saturated or partially unsaturated, also refers to rings that are optionally substituted.

The term "heteroaryl" refers to heteroaromatic ring groups having five to fourteen members. Examples of heteroaryl rings include 2-furanyl, 3-furanyl, 3-furazanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 2-pyrazolyl, 3-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, or benzoisoxazolyl. Also included within the scope of the term "heteroaryl", as it is used herein, is a group in which a heteroatomic ring is fused to one or more aromatic or nonaromatic rings where the radical or point of attachment is on the heteroaromatic ring. Examples include tetrahydroquinolinyl, tetrahydroisoquinolinyl, and pyrido[3,4-d]pyrimidinyl. The term "heteroaryl" also refers to rings that are optionally substituted. The term "heteroaryl" may be used interchangeably with the term "heteroaryl ring" or the term "heteroaromatic". The term "unsaturated heterocycle" is used interchangeably with the term "heteroaryl".

The term "glycosidic functional group" is well known in the art, and is represented in the structural formulae herein as —O-gly. For avoidance of any doubt, however, a "glycosidic functional group" as used herein means a carbohydrate group linked to the main structure via a glycosidic bond. Preferably, the carbohydrate is a sugar. Preferably the sugar is glucose, deoxyglucose, rhamnose or rutinose.

The present invention relates to compounds as defined herein and salts thereof. In one embodiment of this invention, the salts of the compounds are pharmaceutically acceptable salts. Typical examples of salts include hydrohalogenates (for instance, the hydrochloride, hydrobromide, or hydroiodide salt), inorganic acid salts (for instance, the sulphate, nitrate, perchlorate, phosphate, carbonate or bicarbonate salt), organic carboxylic acid salts (for instance, the acetate, maleate, tartrate, fumarate or citrate salt), organic sulfonic acid salts (for instance, the methanesulfonate (mesylate), ethanesulfonate, benzenesulfonate, toluenesulfonate or camphorsulfonate salt), amino acid salts (for instance, the aspartate or glutamate salt), quaternary ammonium salts, alkaline metal salts (for instance, the sodium or potassium salt) and alkaline earth metal salts (for instance, the magnesium or calcium salt).

The compound of the invention of a salt thereof, typically a pharmaceutically acceptable salt thereof, is typically formulated for use with a pharmaceutically acceptable carrier, diluent, excipient and/or vehicle.

In a second aspect, the present invention therefore provides a composition comprising a compound of the invention or a pharmaceutically acceptable salt thereof and a pharmaceutically acceptable carrier, diluent, excipient or vehicle.

Such compositions may be prepared by any method known in the art of pharmacy, for example by admixing the active ingredient with the carrier, diluent, excipient and/or vehicle under sterile conditions.

Suitable carriers, vehicles, adjuvants and/or diluents are well known in the art and include saline, phosphate buffered saline (PBS), carboxymethylcellulose (CMC), methylcellulose, hydroxypropylmethylcellulose (HPMC), dextrose, liposomes, polyvinyl alcohol, pharmaceutical grade starch, mannitol, lactose, magnesium stearate, sodium saccharin, talcum, cellulose, glucose, sucrose (and other sugars), magnesium carbonate, gelatin, oil, alcohol, detergents, emulsifiers or water (preferably sterile). The compound of the invention can be formulated as a liquid formulation, which will generally consist of a suspension or solution of the compound of the invention in a suitable aqueous or non-aqueous liquid carrier or carriers, for example water, ethanol, glycerine, polyethylene glycol (PEG) or an oil.

In a third aspect, the present invention provides a composition of the second aspect of the invention for use in the treatment of a disease or disorder involving oxidative damage.

A "disease or disorder involving oxidative damage" as used herein means any disease or disorder in which oxidative damage plays a role. Such diseases and disorders include cancer, cardiovascular disease (heart disease), ischaemia-reperfusion injury, ischaemic stroke, neurological disorders such as Alzheimer's disease, Parkinson's disease, Huntington's disease, Friedrich's ataxia, neurodegeneration, diabetic complications, neuropathies, amyotrophic lateral sclerosis, septic shock, muscular dystrophy, multiple sclerosis, inflammatory bowel disease, arthritis, mitochondrial dysfunction, renal disease, ophthalmologic conditions, metabolic conditions, psoriasis, haematological diseases, atherosclerosis, hepatitis, non-alcoholic fatty liver disease and HIV/AIDs-related illnesses.

This aspect of the invention also extends to the use of a composition of the second aspect of the invention in the manufacture of a medicament for the treatment of a disease or disorder involving oxidative damage.

This aspect of the invention also extend to a method for the treatment of a disease or disorder involving oxidative damage comprising administering a therapeutic amount of a composition of the second aspect of the invention to a subject in need thereof.

In a fourth aspect, the present invention provides a composition of the second aspect of the invention for preventing UV damage to the skin of a mammal. Typically, the mammal is a human.

This aspect of the invention also extends to the use of a composition of the second aspect of the invention in the manufacture of a medicament for preventing UV damage to the skin of a mammal.

This aspect of the invention also extends to a method of preventing UV damage to the skin of a mammal, comprising administering a therapeutically effective amount of a composition of the second aspect of the invention to a subject in need thereof.

In a fifth aspect, the present invention provides a method of preventing or reversing the effects of ageing, or for treating or preventing dry skin, comprising administering a composition of the second aspect of the invention to a subject in need thereof. This aspect of the invention is typically a cosmetic method. However, the method of this aspect of the invention may be a therapeutic method, for example to treat the effects of premature ageing, for example caused by a disease such as Cockayne syndrome. In this embodiment, this aspect of the invention therefore also extends to a composition of the second aspect of the invention for use in the treatment of premature ageing. This aspect of the invention also extends to the use of a composition of the second aspect of the invention in the manufacture of a medicament for the treatment of premature ageing.

The composition of the second aspect of the invention can be administered alone or together with another agent.

The composition of the second aspect of the invention is typically administered to a subject in a therapeutically effective amount. Such an amount is an amount effective to ameliorate, eliminate or prevent one or more symptoms of a disease or disorder involving oxidative damage. Preferably, the subject to be treated is a human. However, the present invention is equally applicable to human or veterinary medicine. For example, the present invention may find use in treating companion animals, such as dogs and cats, or working animals, such as race horses.

The term "treatment", within the scope of the present invention, is intended to include prophylactic and therapeutic treatment.

The composition of the second aspect of the invention can be administered to the subject by any suitable means. The composition of the second aspect of the invention can be administered systemically, in particular intra-articularly, intra-arterially, intraperitoneally (i.p.), intravenously or intramuscularly. However, the composition of the second aspect of the invention can also be administered by other enteral or parenteral routes such as by subcutaneous, intradermal, topical (including buccal, sublingual or transdermal), oral (including buccal or sublingual), nasal, vaginal, anal, pulmonary or other appropriate administration routes. In the fifth aspect of the invention, the composition of the second aspect of the invention is typically administered topically.

Pharmaceutical compositions adapted for oral administration may be presented as discrete units such as capsules or tablets; as powders or granules; as solutions, syrups or suspensions (in aqueous or non-aqueous liquids; or as edible foams or whips; or as emulsions). Suitable excipients for tablets or hard gelatine capsules include lactose, maize starch or derivatives thereof, stearic acid or salts thereof. Suitable excipients for use with soft gelatine capsules include for example vegetable oils, waxes, fats, semi-solid, or liquid polyols etc. For the preparation of solutions and syrups, excipients which may be used include for example water, polyols and sugars. For the preparation of suspensions, oils (e.g. vegetable oils) may be used to provide oil-in-water or water in oil suspensions.

Pharmaceutical compositions adapted for topical administration may be formulated as ointments, creams, suspensions, lotions, powders, solutions, pastes, gels, sprays, aerosols or oils. For infections of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles and mouth washes.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research*, 3(6):318 (1986).

Pharmaceutical compositions adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable compositions wherein the carrier is a liquid, for administration as a nasal spray or as nasal drops, include aqueous or oil solutions of the active ingredient.

Pharmaceutical compositions adapted for administration by inhalation include fine particle dusts or mists which may be generated by means of various types of metered dose pressurised aerosols, nebulizers or insufflators.

Pharmaceutical compositions adapted for rectal administration may be presented as suppositories or enemas.

Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solution which may contain anti-oxidants, buffers, bacteriostats and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerine and vegetable oils, for example. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets.

The pharmaceutical compositions may contain preserving agents, solubilising agents, stabilising agents, wetting agents, emulsifiers, sweeteners, colourants, odourants, salts, buffers, coating agents or antioxidants.

The dose of the composition of the second aspect of the invention to be administered may be determined according to various parameters, especially according to the compound of the invention used; the age, weight and condition of the patient to be treated; the route of administration; and the required regimen. A physician will be able to determine the required route of administration and dosage for a particular patient.

This dosage may be repeated as often as appropriate. If side effects develop the amount and/or frequency of the dosage can be reduced, in accordance with normal clinical practice.

For administration to mammals, and particularly humans, it is expected that the daily dosage of the active agent will be from 1 µg/kg to 10 mg/kg body weight, typically around 10 µg/kg to 1 mg/kg body weight. The physician in any event will determine the actual dosage which will be most suitable for an individual which will be dependant on factors including the age, weight, sex and response of the individual. The above dosages are exemplary of the average case. There can, of course, be instances where higher or lower dosages are merited, and such are within the scope of this invention.

The compounds of the present invention are antioxidant compounds and therefore find use in protecting cells against oxidative stress and free radical damage in vitro.

Accordingly, in a sixth aspect, the present invention provides a compound of Formula I or a salt thereof for use in protecting cells against oxidative stress and free radical damage in vitro. This aspect of the invention also extends to a method for protecting a cell against oxidative stress and free radical damage in vitro comprising contacting a cell with a compound of Formula I or a salt thereof. The methods of this aspect of the present invention are typically carried out in vitro or ex vivo.

In one embodiment, the cell is contacted with the compound of Formula I or a salt thereof by adding the compound or salt to the culture medium in which the cell is grown in vitro.

The methods of this aspect of the invention can comprise contacting the cell with one or more compounds of Formula I or salts thereof. Typically, the cell is contacted with a compound of Formula I or a salt thereof, or with a combination of 2, 3, 4, 5, 6 or more compounds of Formula I or salts thereof.

The cell can be any type of cell or cell line, for example undifferentiated cells such as stem cells, re-programmed cells, progenitor cells, differentiated cells, human and animal cell lines.

Undifferentiated cells for use in the method of this aspect of the invention are typically stem cells, for example totipotent stem cells (capable of differentiating into embryonic and extraembryonic cell types), pluripotent stem cells (capable of differentiating into endoderm, mesoderm and ectoderm germ layers), and multipotent stem cells (capable of differentiating into a plurality of closely related cells). Types of stem cells for use in the method of this aspect of the invention include embryonic stem (ES) cells (ESCs), adult stem cells and induced pluripotent stem (iPS) cells.

Embryonic stem cells are derived from the blastocyst of a mammalian embryo and are totipotent. Embryonic stem cells were originally described by Evans and Kaufman (Nature, 292(5819): 154-156, 1981). Adult stem cells are pluripotent, and include hematopoietic stem cells and mesenchymal stem cells. Induced pluripotent cells are artificially derived from a non-pluripotent cell such as an adult somatic cell by the insertion of certain genes and are very similar to embryonic stem cells (Takahashi et al, Cell 131(5): 861-872, 2007; and Yu et al, Science 318(5858), 1917-1920, 2007). Stem cells are also found in the blood of the umbilical cord.

Stem cells for use in the method of this aspect of the invention can be human or non-human. Typically, the stem cell is a mouse or human embryonic stem cell. Typically, such human embryonic stem cells are derived from an established stem cell line.

In one embodiment, the cell is part of a tissue or organ.

This aspect of the invention finds particular use in the protection of tissues and/or organs for transplantation, for example when said tissue or organ is being stored prior to transplantation and to protect the said tissue or organ from ensuing oxidative stress and free radical damage post transplantation, for example as a result of reperfusion injury. In this embodiment, tissues or organs can be treated with the compound of Formula I or a salt thereof after removal from a donor and prior to being transplanted into a recipient.

This aspect of the invention is also related to the second aspect of the invention which relates to a composition of the invention for use in the treatment of a disease or disorder involving oxidative damage. In one embodiment, the disease or disorder involving oxidative damage is ischaemia-reperfusion injury, which can occur for example after transplantation of a tissue or organ to a recipient. In this embodiment, the composition of the invention is administered to the recipient of the transplant in order to protect the recipient from ischaemia-reperfusion injury.

Preferred features for the second and subsequent aspects of the invention are as for the first aspect mutatis mutandis.

The present invention will now be further described by way of reference to the following Examples which are present for the purposes of illustration only. In the Examples, reference is made to a number of Figures in which.

EXAMPLES

Example 1

Synthesis of AO3003

Figure 1:
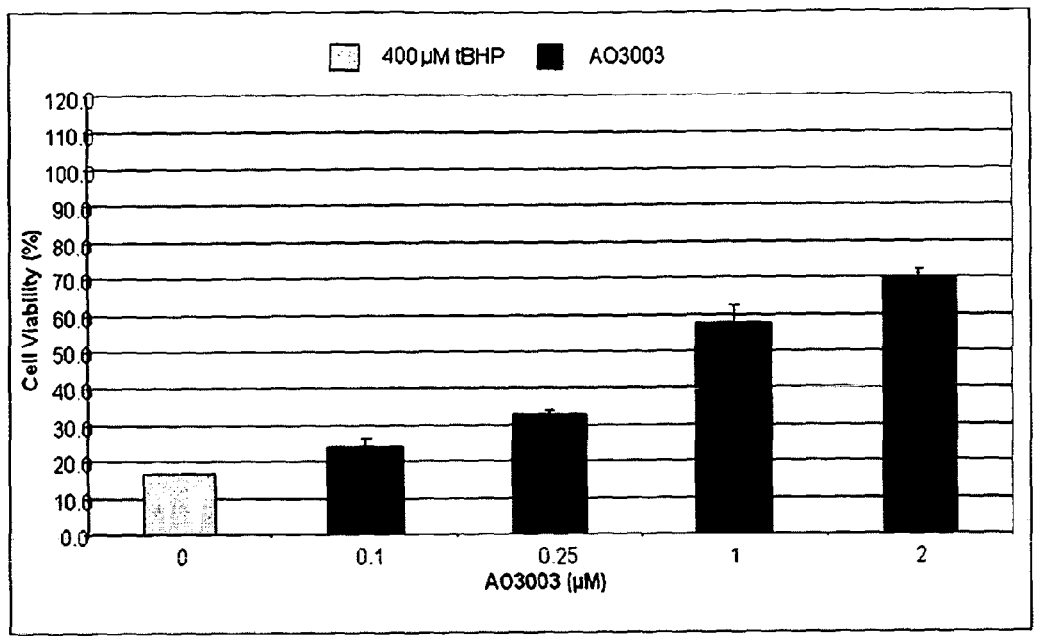
FIG. 1 shows protection of mouse embryonic stem cells against 4.5 h oxidative challenge by tert Butyl hydroperoxide (tBHP) by incubating with or without AO3003 in the medium added 30 min prior to exposure.

The compound AO3003 having the following structure was synthesised as follows.

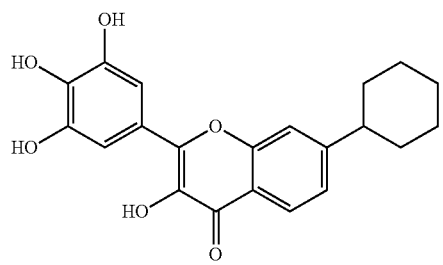 [SMILES: O=c1c(O)c(-c2cc(O)c(O)c(O)c2)oc2cc(C3CCCCC3)ccc12]

Steps 1, 3 and 4 are described in WO 2004/007475.

Step 1: Synthesis of 2-hydroxy-4-iodo-acetophenone

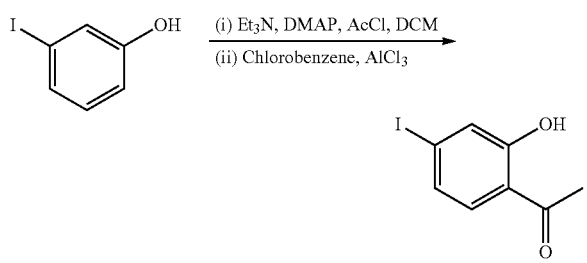

Step 2: Synthesis of 4-benzyloxy-3,5-dimethoxy-benzaldehyde by reaction of 4-hydroxy-3,5-dimethoxybenzaldehyde (Syringealdehyde) (Sigma-Aldrich) and Benzyl Bromide (Sigma-Aldrich)

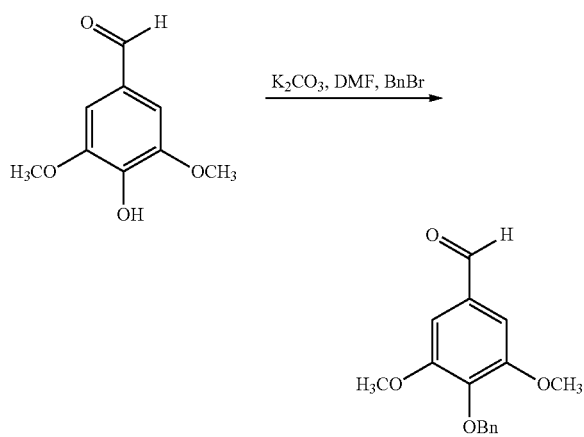

Step 3: Synthesis of 2'-hydroxy-4'-iodo-4-benzyloxy-3,5-dimethoxy-chalcone

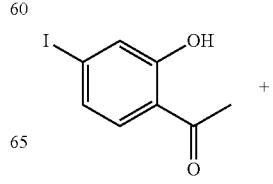

+

-continued
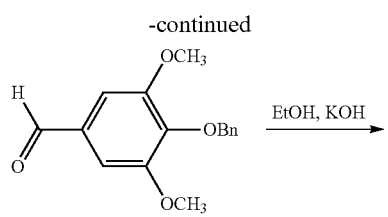
EtOH, KOH
Step 4: Synthesis of 3-benzyloxy-7-iodo-2-(4-benzyloxy-3,5-dimethoxy-phenyl)-chromen-4-one
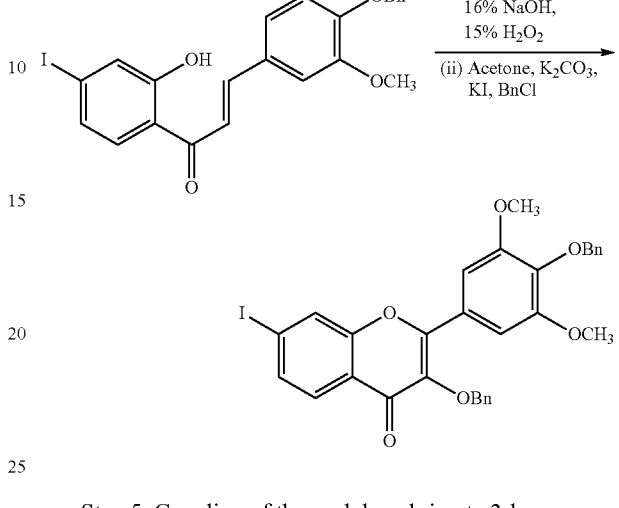
(i) MeOH, 16% NaOH, 15% $H_2O_2$
(ii) Acetone, $K_2CO_3$, KI, BnCl
Step 5: Coupling of the cyclohexyl ring to 3-benzyloxy-7-iodo-2-(4-benzyloxy-3,5-dimethoxy-phenyl)-chromen-4-one
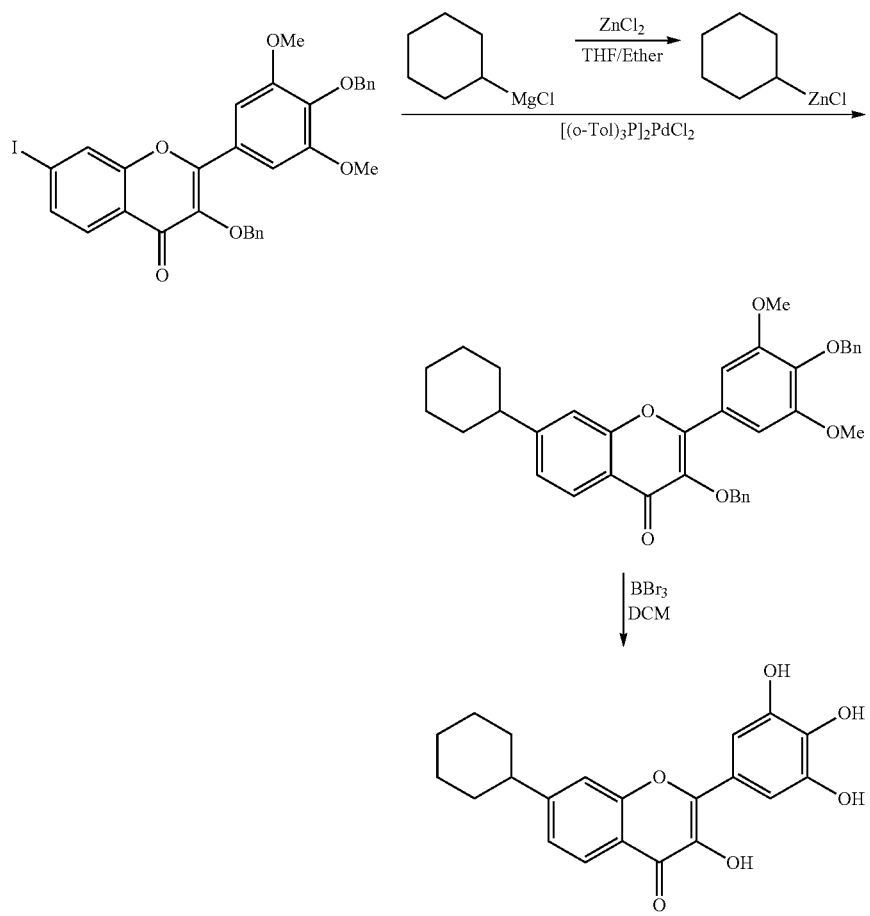

Negishi Coupling

To a 50 ml three-necked flask was charged anhydrous THF (10 ml) and 2 M cyclohexylmagnesium chloride in diethyl ether (4 ml, 8 mmol). The mixture was stirred under $N_2$ and cooled to 0° C. 1 M $ZnCl_2$ in diethyl ether (8 ml, 8 mmol) was added dropwise at <10° C. The whole mixture was then stirred at room temperature for 1 hour. Iodoflavonoid (400 mg, 0.64 mmol) and $[(o-Tol)_3P]_2PdCl_2$ (50 mg) were added. The mixture was heated to reflux for 3 hours before cooling to room temperature overnight. LCMS showed no starting material remaining but with a major peak @6.719 min (36.1%). The mixture was poured onto 3N HCl (60 ml) and extracted with DCM (3×60 ml). The organic layers were combined, dried over $MgSO_4$, filtered and concentrated in vacuo to afford a dark brown oil (560 mg). The crude material was purified by column using silica (96 g), eluting with 20% ethyl acetate in heptane to afford two fractions: A (60 mg) and B (93 mg). $^1$H nmr and LCMS showed that Fraction A contained ~40% of desired product and Fraction B contained ~80% of mono-debenzylated product.

$BBr_3$ Deprotection

To a 50 ml flask was charged Fraction B (93 mg and DCM (5 ml). The mixture was stirred under $N_2$ and cooled to 0° C. 1 M $BBr_3$ in DCM (1.6 ml) was added dropwise at 0° C. The whole mixture was warmed to room temperature and stirred overnight. LCMS showed no starting material remaining and 86.2% of product. The mixture was cooled to 0° C. and methanol (10 ml) was added. The mixture was heated to reflux for 2 hours before being concentrated in vacuo. Purification by prep-HPLC afforded final product (AO3003) with LC purity of 97.5%.

Example 2

AO3003 Protects Against Oxidative Stress mES Cell Culture

The mouse embryonic stem cell line E14Tg2a was maintained in a pluripotent state in knockout (KO) DMEM supplemented with leukaemia inhibitory factor (LIF), 15% (v/v) knockout serum replacement, 0.1 mM MEM non-essential amino acids, 2 mM 1-glutamine and 140 µM 2-mercaptoethanol in tissue culture flasks coated with 0.1% (w/v) gelatin.

MIN-6 Cell Culture

The mouse β-cell insulinoma line MIN-6 was maintained in high glucose DMEM supplemented with 15% heat-inactivated foetal bovine serum (FBS) and 70 µM 2-mercaptoethanol.

Methods

Experiment 1 mES cells were plated into a 0.1% (w/v) gelatin coated 96-well tissue culture plate at a density of $1.5 \times 10^4$ cells per well. The cells were cultured at 37° C. in an atmosphere of 5% $CO_2$ for 20-24 hours before the addition of AO3003, 30 minutes prior to the onset of the tert-butyl hydroperoxide (tBHP) challenge. The cells were incubated with tBHP for 90 minutes at 37° C. (5% $CO_2$) before 20 µl 5 mg/ml 3-(4,5-Dimethyl-2-thiazolyl)-2,5-diphenyl-2H-tetrazolium bromide (MTT) was added to each of the treatment wells. The cells were incubated for a further 3 hours at 37° C. (5% $CO_2$) before all the supernatant was removed from the cells and the insoluble MTT formazan dye, produced by the reduction of MTT by viable cells, was solubilised in 200 µl dimethyl sulfoxide (DMSO). The absorbance of the resulting solution was measured at 540 nm and was proportional to the number of viable mES cells remaining after the tBHP challenge. The results are shown in FIG. 1.

Figure 2:
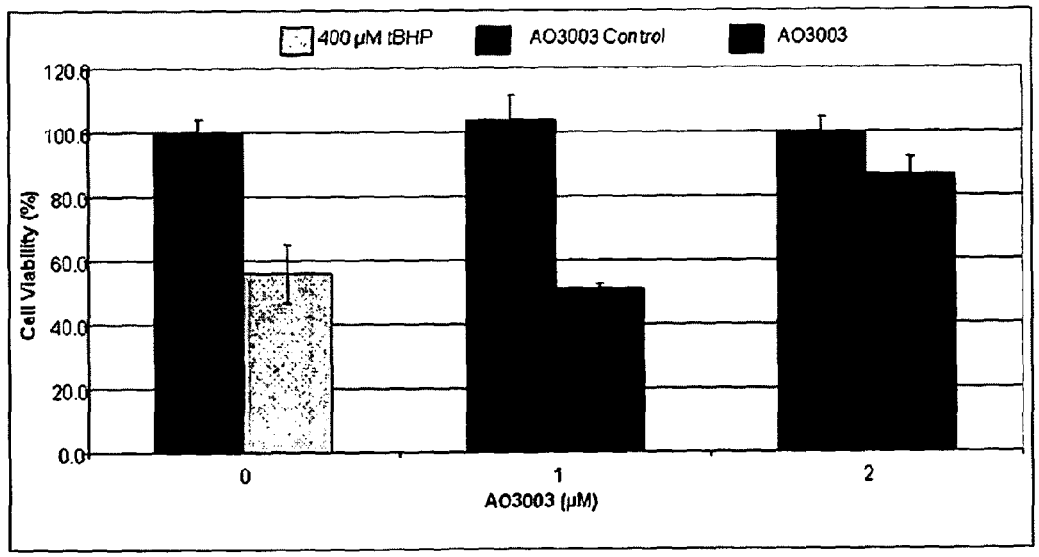
FIG. 2 shows protection of mouse embryonic stem cells against 4.5 h oxidative challenge by tert Butyl hydroperoxide induced 24.5 h after uptake of AO3003 into the cells.

Experiment 2 mES cells were plated into a 0.1% (w/v) gelatin coated 96-well tissue culture plate at a density of $7.5 \times 10^3$ cells per well. The cells were cultured at 37° C. in an atmosphere of 5% $CO_2$ for 20-24 hours before the addition of AO3003, 20 hours prior to the onset of the tert-butyl hydroperoxide (tBHP) challenge. The cells were incubated with tBHP for 90 minutes at 37° C. (5% $CO_2$) before 20 µl 5 mg/ml 3-(4,5-Dimethyl-2-thiazolyl)-2,5-diphenyl-2H-tetrazolium bromide (MTT) was added to each of the treatment wells. The cells were incubated for a further 3 hours at 37° C. (5% $CO_2$) before all the supernatant was removed from the cells and the insoluble MIT formazan dye, produced by the reduction of MTT by viable cells, was solubilised in 200 µl dimethyl sulfoxide (DMSO). The absorbance of the resulting solution was measured at 540 nm and was proportional to the number of viable mES cells remaining after the tBHP challenge. The results are shown in FIG. 2.

At 2 µM, AO3003 significantly reverses oxidative stress-induced loss of viability. This indicates that, once incorporated into the cell, AO3003 remains bioprotective for a period >24 h. The controls show cell viability at 24 h after 0, 1 and 2 µM exposure to AO3003 indicating that the compound is not toxic at the bioprotective concentration.

Experiment 3

Figure 3:
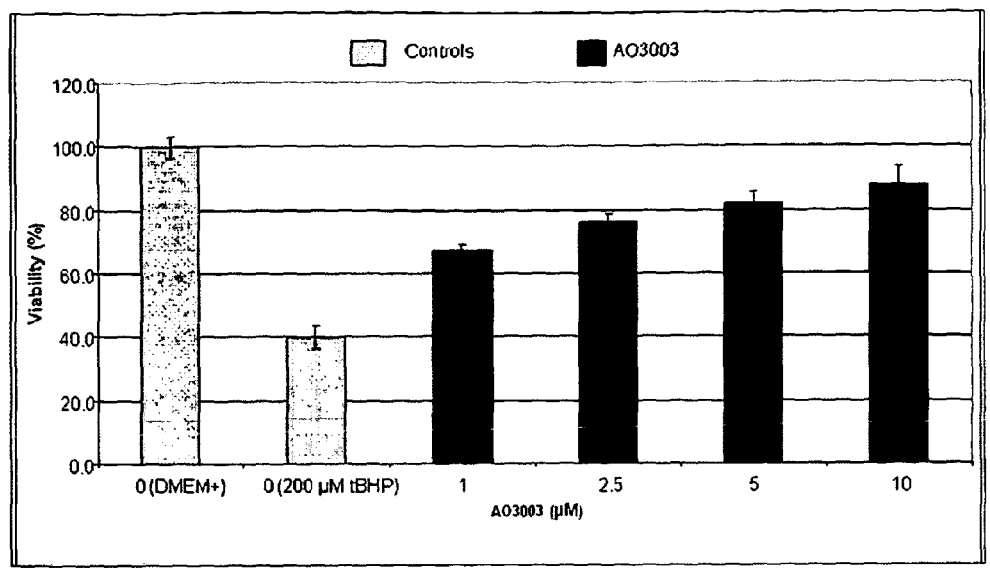
FIG. 3 shows protection of MIN6 insulinoma cell line against 4.5 h oxidative challenge by tert Butyl hydroperoxide by incubating with or without AO3003 in the medium added 30 min prior to exposure. DMEM is the control viability of cells without peroxide or tBHP.

MIN-6 cells were plated into a 96-well tissue culture plate at a density of $2.0 \times 10^4$ cells per well. The cells were cultured at 37° C. in an atmosphere of 5% $CO_2$ for 20-24 hours before the addition of AO3003, 30 minutes prior to the onset of the tert-butyl hydroperoxide (tBHP) challenge. The cells were incubated with tBHP for 30 minutes at 37° C. (5% $CO_2$) before 20 µl 5 mg/ml 3-(4,5-Dimethyl-2-thiazolyl)-2,5-diphenyl-2H-tetrazolium bromide (MTT) was added to each of the treatment wells. The cells were incubated for a further 3 hours at 37° C. (5% $CO_2$) before all the supernatant was removed from the cells and the insoluble MTT formazan dye, produced by the reduction of MIT by viable cells, was solubilised in 200 µl dimethyl sulfoxide (DMSO). The absorbance of the resulting solution was measured at 540 nm and was proportional to the number of viable mES cells remaining after the tBHP challenge. The results are shown in FIG. 3. DMEM is the control viability of cells without peroxide or tBHP.

In summary, the results show that the compound AO3003 protects against oxidative stress in a mouse embryonic stem cell line and a mouse insulinoma cell line.

Example 3

Synthesis of AO-CHA

Stage 1

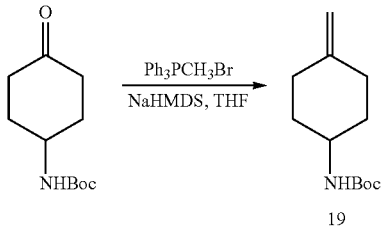

To a slurry of PH₃PCH₃Br (4.21 g) and THF (10 ml) at 0° C. was added NaHMDS (11.8 ml, 1M in THF) at <5° C. The resulting yellow solution was stirred for 1 h before addition of a solution of N-Boc-4-aminocyclohexanone (2 g) in THF (10 ml) at 0-5° C. After stirring for 4 h at room temperature, TLC showed no starting material remained. Water (20 ml) and brine (20 ml) were added followed by EtOAc (40 ml). The organic layer was separated, dried (MgSO₄), filtered and adsorbed onto silica (6 g). Purification by column chromatography on silica (80 g), eluting with 4:1 heptane:EtOAc gave 19 as a white solid (>95% by ¹H NMR, 71% yield).

Stage 2

Synthesis of 3-benzyloxy-7-iodo-2-(4-benzyloxy-3,5-dimethoxy-phenyl)-chromen-4-one was Achieved as Described in Example 1

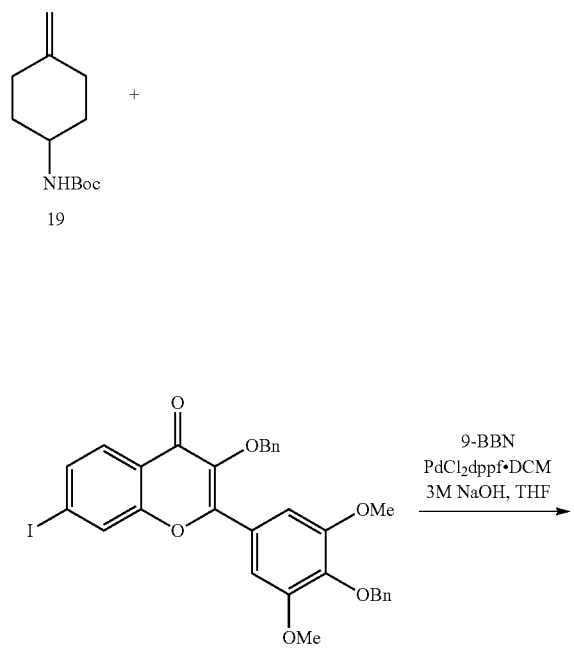

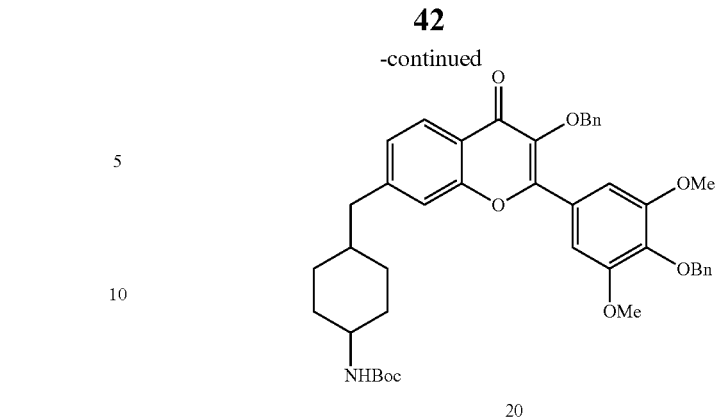

To a solution of 19 (0.68 g) in THF (2 ml) at 0° C. was added 9-BBN (6.44 ml, 0.5M in THF), after 5 h at room temperature, 3M NaOH (0.8 ml) was added [POT A]. In a separate vessel was added THF (3 ml), iodoflavonone (1.0 g) and PdCl₂ddpf.DCM (50 mg) at 0° C. [POT B]. [POT A] was added to [POT B] at <5° C. and the reaction stirred room temperature overnight. LCMS indicated 62% stage 2. The THF was removed in vacuo and the residue was partitioned between water (20 ml) and DCM (30 ml). The organic layer was separated (phase separator) and adsorbed onto silica (4 g). The material was purified by column chromatography on silica (30 g), eluting with 4:1 to 3:1 heptane:EtOAc. This gave 602 mg 20 (>95 by NMR, 53% yield).

Stage 3

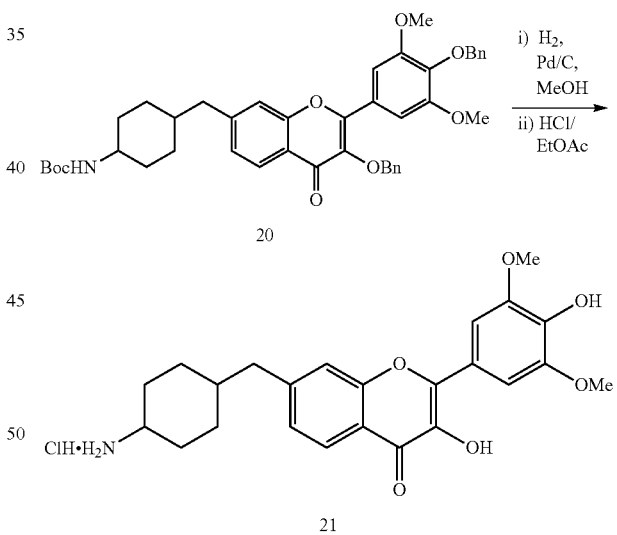

20 (600 mg) was dissolved in MeOH (60 ml) at 40° C. and then 10% Pd/C (150 mg, 50% wet) was added and the mixture hydrogenated (1 atm) overnight. LCMS indicated 96% product. The solids were filtered off through Celite and the filtrate concentrated in vacuo to give 435 mg of an orange solid (>95% by NMR).

The solid was dissolved in EtOAc (60 ml) and 4M HCl in EtOAc (20 ml) was charged. After an overnight stir out, the solids were filtered off under N₂ and washed with EtOAc (20 ml). Compound 21 was isolated as an orange solid (255 mg), >95% by NMR, >98% by LCMS (mixture of cis/trans isomers), 65% yield.

Example 4

Activity Studies on AO3003 and AO-CHA

The compound AO3003 has the following structure, as set out above in Example 1:

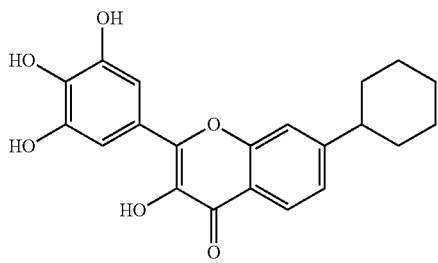 [SMILES: O=c1c(O)c(-c2cc(O)c(O)c(O)c2)oc2cc(C3CCCCC3)ccc12]

The compound AO-CHA has the following structure:

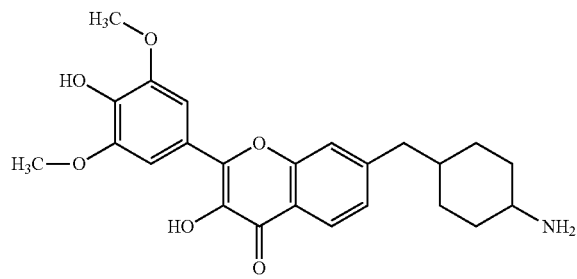 [SMILES: COc1cc(-c2oc3cc(CC4CCC(N)CC4)ccc3c(=O)c2O)cc(OC)c1O]

Cell Culture

The human pancreatic carcinoma cell line was maintained in high glucose DMEM supplemented with 10% heat-inactivated foetal bovine serum (FBS).

The human renal clear cell carcinoma cell line was maintained in RPMI 1640 supplemented with 2 mM L-Glutamine, 1 mM sodium pyruvate and 10% heat-inactivated foetal bovine serum (FBS).

Figure 4:
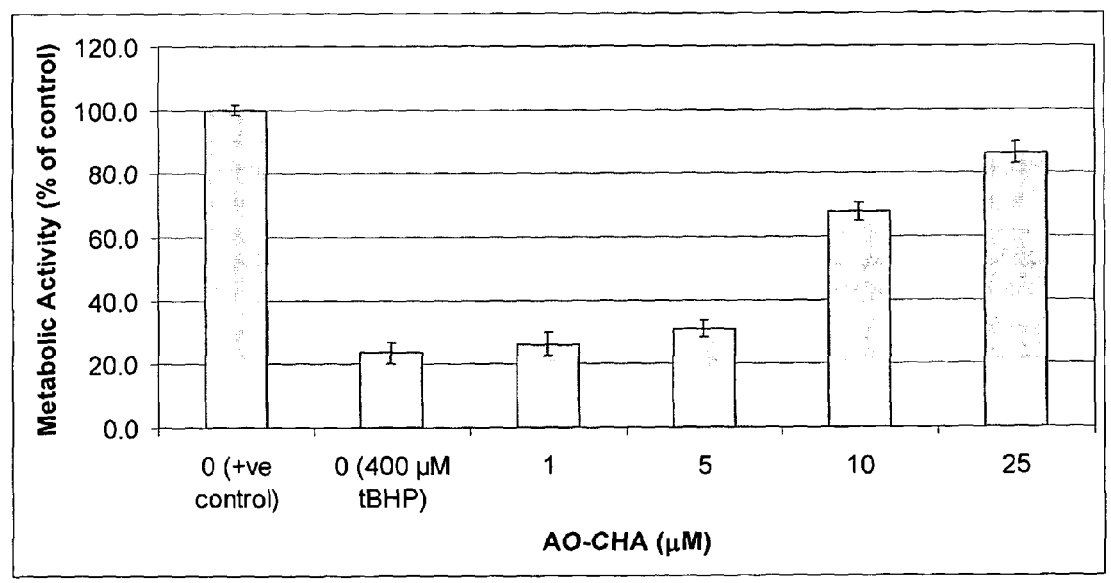
FIG. 4 shows activity of AO-CHA against tBHP-challenge in mouse embryonic stem cells (MTT assay).

Experiment 1: Activity of AO-CHA Against tBHP-Challenge in Mouse Embryonic Stem (mES) Cells—MTT Assay mES cells were plated into a 0.1% (w/v) gelatin coated 96-well tissue culture plate at a density of $2 \times 10^4$ cells per well. The cells were cultured at 37° C. in an atmosphere of 5% $CO_2$ for 20-24 hours before the addition of AO-CHA, 30 minutes prior to the onset of the tert-butyl hydroperoxide (tBHP) challenge. The cells were incubated with tBHP for 60 minutes at 37° C. (5% $CO_2$) before 20 µl 5 mg/ml 3-(4,5-Dimethyl-2-thiazolyl)-2,5-diphenyl-2H-tetrazolium bromide (MTT) was added to each of the treatment wells. The cells were incubated for a further 3 hours at 37° C. (5% $CO_2$) before all the supernatant was removed from the cells and the insoluble MTT formazan dye, produced by the reduction of MTT by viable cells, was solubilised in 200 µl dimethyl sulfoxide (DMSO). The absorbance of the resulting solution was measured at 570 nm and was proportional to the number of viable mES cells remaining after the tBHP challenge. The results are shown in FIG. 4.

Figure 5:
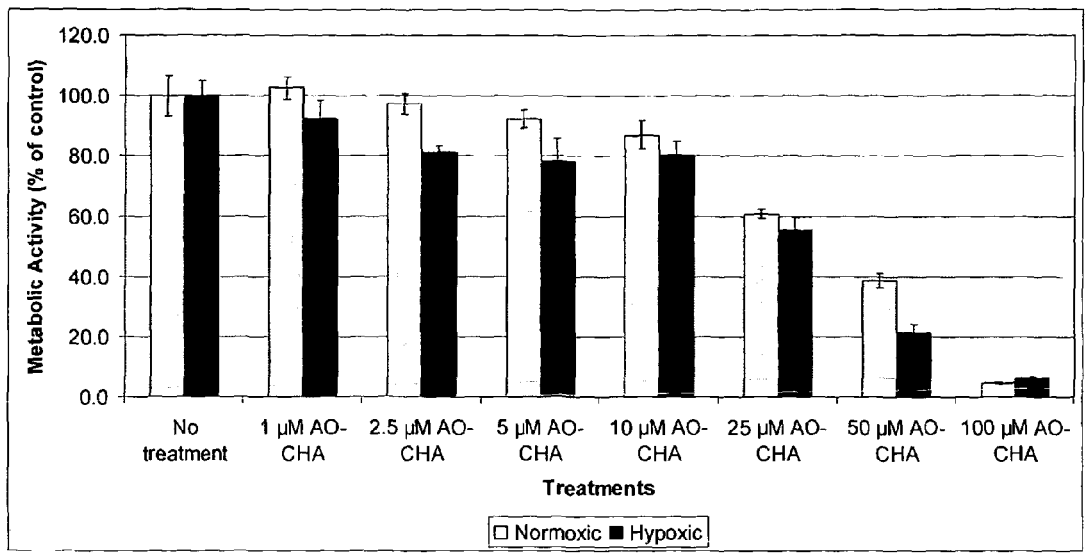
FIG. 5 shows anticancer activity of AO-CHA in pancreatic cancer cell line under normoxic conditions and 1% O2 after 48 h (MTT).

Experiment 2: AO-CHA Anticancer Activity in a Pancreatic Cancer Cell Line Under Normoxic Conditions and Hypoxic 1% $O_2$ after 48 h—MTT Assay Cells were plated into two 96-well tissue culture plates at a density of $6.5 \times 10^3$ cells per well. The cells were cultured at 37° C. in an atmosphere of 5% $CO_2$ for 20-24 hours before the addition of AO-CHA. The cells were incubated at 37° C. in an atmosphere of 5% $CO_2$ and either 1% (hypoxic) or 19% (normoxic) oxygen for 45 hours before 20 µl 5 mg/ml 3-(4,5-Dimethyl-2-thiazolyl)-2,5-diphenyl-2H-tetrazolium bromide (MTT) was added to each of the treatment wells. The cells were incubated for a further 3 hours in the relevant oxygen conditions before all the supernatant was removed from the cells and the insoluble MTT formazan dye, produced by the reduction of MTT by viable cells, was solubilised in 200 µl dimethyl sulfoxide (DMSO). The absorbance of the resulting solution was measured at 570 nm and was proportional to the number of viable cells remaining after culture in the different oxygen conditions. The results are shown in FIG. 5.

Figure 6:
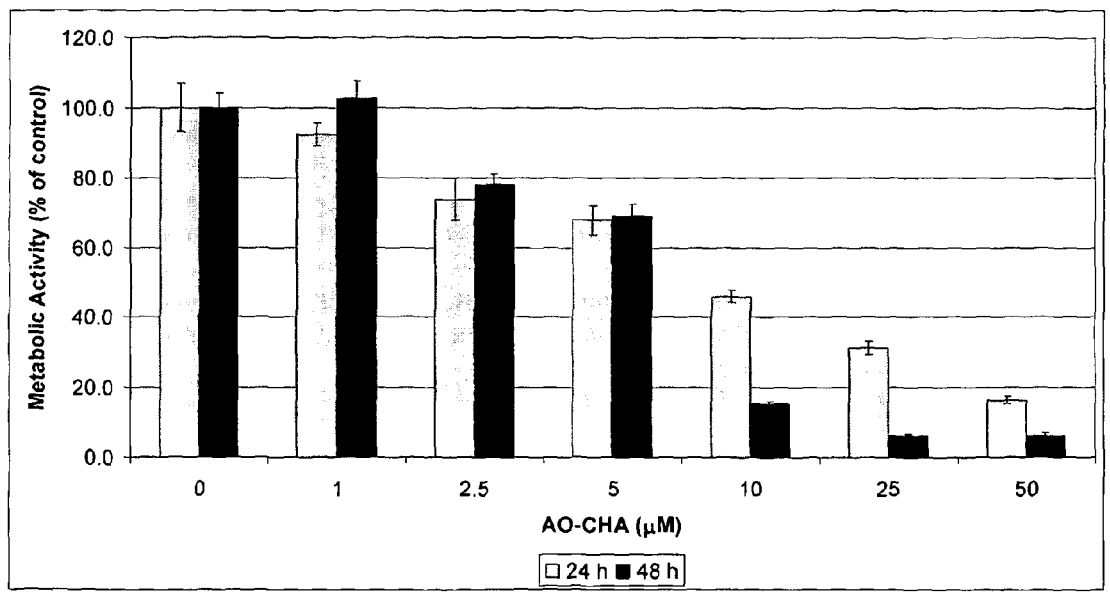
FIG. 6 shows anticancer activity of AO-CHA in a renal carcinoma cell line over 48 h (MTT assay).

Experiment 3: Anticancer Activity of AO-CHA in a Renal Carcinoma Cell Line Over 48 h—MTT Assay Cells were plated into two 96-well tissue culture plates at a density of $2.5 \times 10^3$ cells per well. The cells were cultured at 37° C. in an atmosphere of 5% $CO_2$ for 20-24 hours before the addition of AO-CHA. The cells were incubated for either 21 or 45 hours at 37° C. (5% $CO_2$) before 20 µl 5 mg/ml 3-(4,5-Dimethyl-2-thiazolyl)-2,5-diphenyl-2H-tetrazolium bromide (MTT) was added to each of the treatment wells. The cells were incubated for a further 3 hours at 37° C. (5% $CO_2$) before all the supernatant was removed from the cells and the insoluble MIT formazan dye, produced by the reduction of MIT by viable cells, was solubilised in 200 µl dimethyl sulfoxide (DMSO). The absorbance of the resulting solution was measured at 570 nm and was proportional to the number of viable cells remaining after AO-CHA treatment. The results are shown in FIG. 6.

Figure 7:
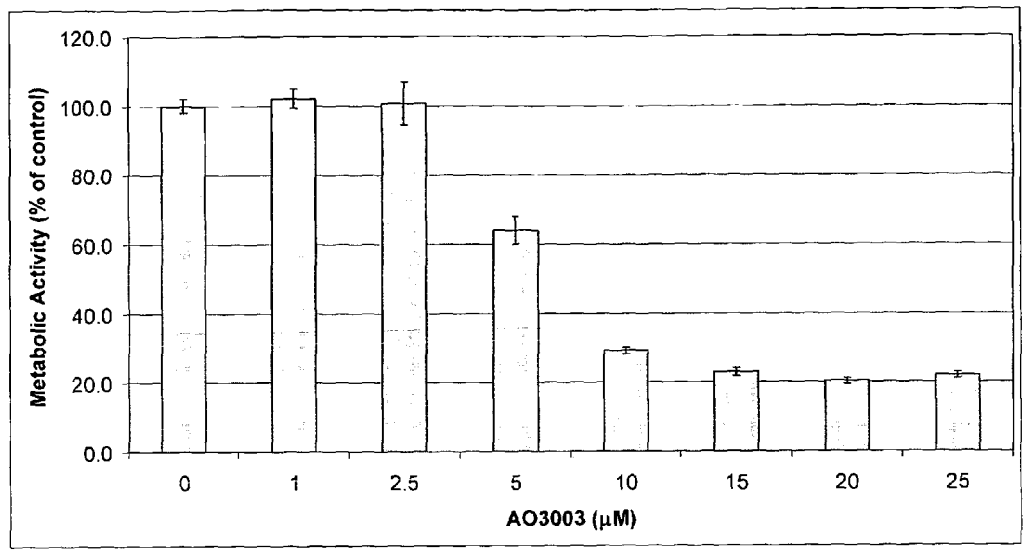
FIG. 7 shows anticancer activity of AO-3003 in renal cancer cell line after 48 h (MTT assay).

Experiment 4: Anticancer Activity of AO-3003 in a Renal Carcinoma Cell Line after 48 h—MTT Assay Cells were plated into a tissue culture plate at a density of $2.5 \times 10^3$ cells per well. The cells were cultured at 37° C. in an atmosphere of 5% $CO_2$ for 20-24 hours before the addition of AO-3003. The cells were incubated for 45 hours at 37° C. (5% $CO_2$) before 20 µl 5 mg/ml 3-(4,5-Dimethyl-2-thiazolyl)-2,5-diphenyl-2H-tetrazolium bromide (MTT) was added to each of the treatment wells. The cells were incubated for a further 3 hours at 37° C. (5% $CO_2$) before all the supernatant was removed from the cells and the insoluble MTT formazan dye, produced by the reduction of MTT by viable cells, was solubilised in 200 µl dimethyl sulfoxide (DMSO). The absorbance of the resulting solution was measured at 570 nm and was proportional to the number of viable cells remaining after AO-CHA treatment. The results are shown in FIG. 7.

Figure 8:
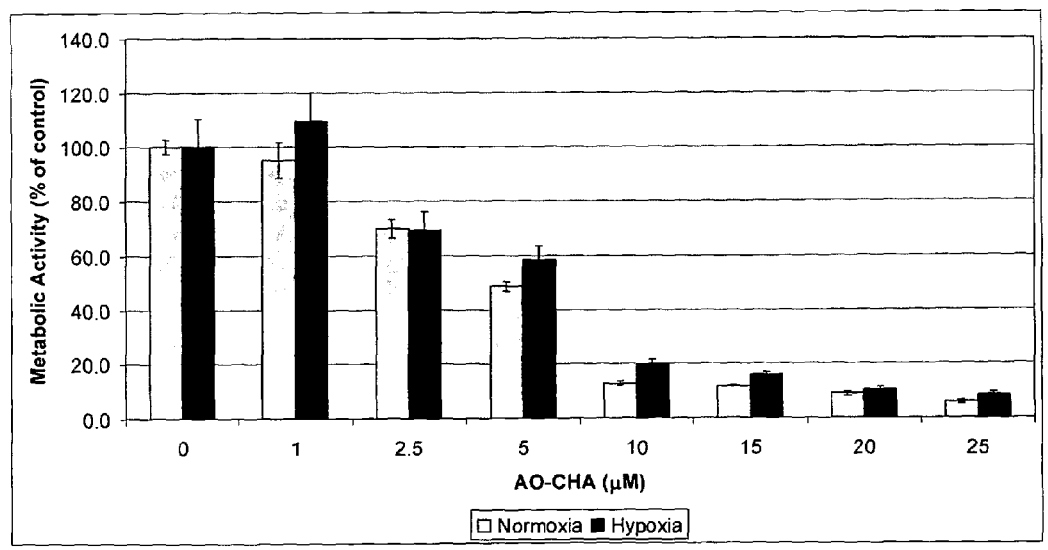
FIG. 8 shows anticancer activity of AO-CHA in renal cancer cell line under normoxic conditions and 2% O2 after 48 h (MTT assay).

Experiment 5: AO-CHA Anticancer Activity in a Renal Carcinoma Cell Line Under Normoxic Conditions and Hypoxic 2% $O_2$ after 48 h—MTT Assay Cells were plated into two 96-well tissue culture plates at a density of $2.5 \times 10^3$ cells per well. The cells were cultured at 37° C. in an atmosphere of 5% $CO_2$ for 20-24 hours before the addition of AO-CHA. The cells were incubated at 37° C. in an atmosphere of 5% $CO_2$ and either 2% (hypoxic) or 19% (normoxic) oxygen for 45 hours before 20 µl 5 mg/ml 3-(4,5-Dimethyl-2-thiazolyl)-2,5-diphenyl-2H-tetrazolium bromide (MTT) was added to each of the treatment wells. The cells were incubated for a further 3 hours in the relevant oxygen conditions before all the supernatant was removed from the cells and the insoluble MIT formazan dye, produced by the reduction of MTT by viable cells, was solubilised in 200 µl dimethyl sulfoxide (DMSO). The absorbance of the resulting solution was measured at 570 nm and was proportional to the number of viable cells remaining after culture in the different oxygen conditions. The results are shown in FIG. 8.

Figure 9:
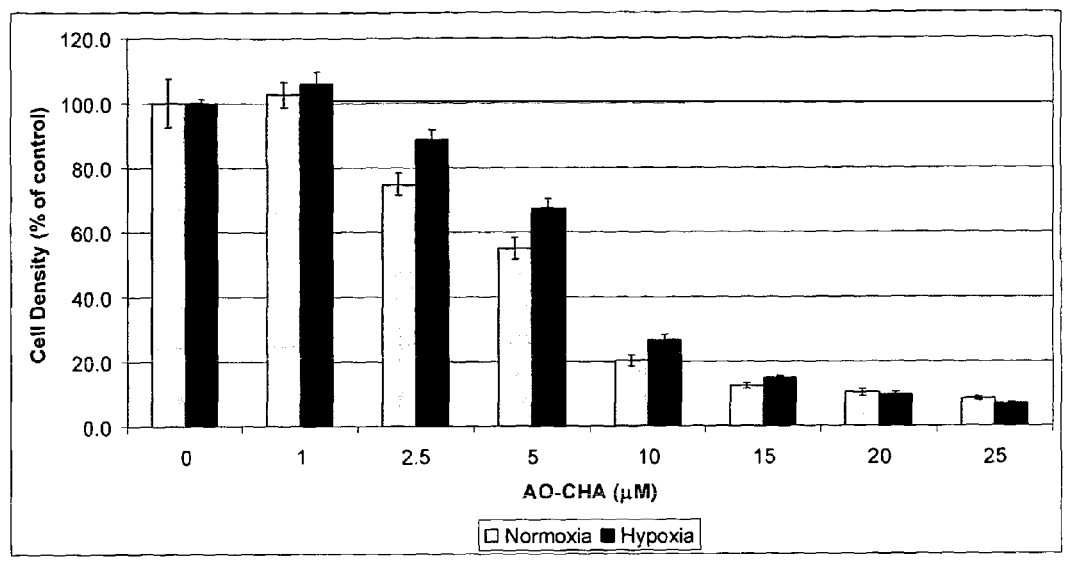
FIG. 9 shows anticancer activity of AO-CHA in renal cancer cell line under normoxic conditions and 2% O2 after 48 h (SRB assay).

Experiment 6: AO-CHA Anticancer Activity in a Renal Carcinoma Cell Line Under Normoxic Conditions and hypoxic 2% $O_2$ after 48 h—SRB Assay Cells were plated into two 96-well tissue culture plates at a density of $2.5 \times 10^3$ cells per well. The cells were cultured at 37° C. in an atmosphere of 5% $CO_2$ for 20-24 hours before the addition of AO-CHA. The cells were incubated at 37° C. in an atmosphere of 5% $CO_2$ and either 2% (hypoxic) or 19% (normoxic) oxygen for 48 hours before the cells were fixed by addition of 50 µl cold 25% Trichloro-acetic acid (TCA) for 60 minutes. Cells were stored at 4° C. during fixation. TCA removed from cells and wells were washed gently ten times under running tap water. Cells dried and 50 µl 0.4% Sulphorhodamine B (SRB) added to each treatment well then the cells were incubated at room temperature for 30 minutes. SRB removed and wells were washed four times at room temperature with 1% glacial acetic acid. Cells dried and 150 µl of 10 mM Tris buffer (pH 10.5) was added to each treatment well. The plate was left on a shaking platform at room temperature for 60 minutes and the absorbance of the resulting solution was measured at 570 nm and was proportional to the cell density of the remaining cells after treatment. The results are shown in FIG. 9.

Figure 10:
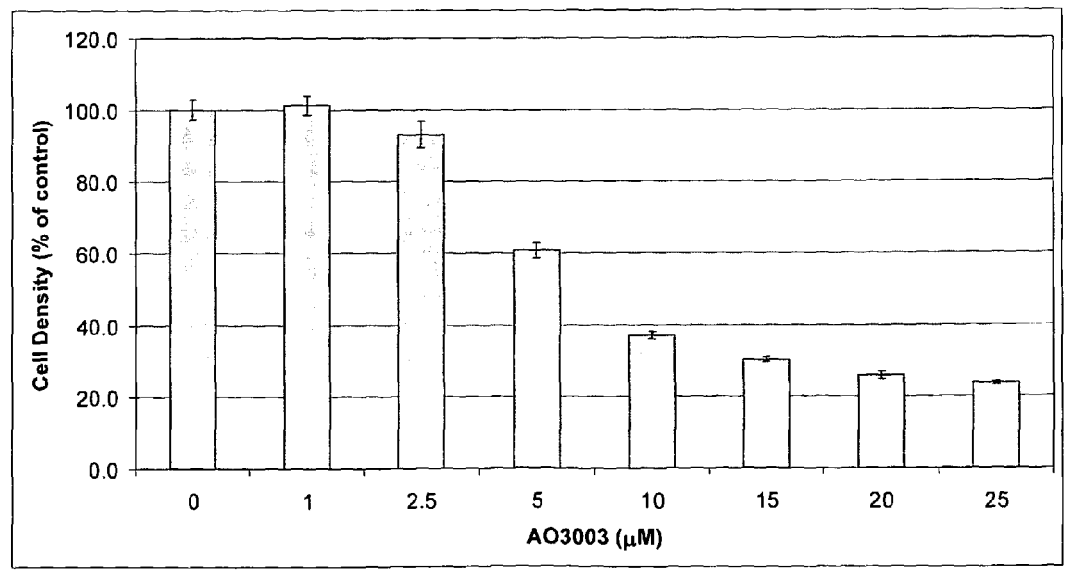
FIG. 10 shows anticancer activity of AO-3003 in renal cancer cell line after 48 h (SRB assay).

Experiment 7: AO-3003 Anticancer Activity in a Renal Carcinoma Cell Line after 48 h—SRB Assay Cells were plated into a tissue culture plate at a density of $2.5 \times 10^3$ cells per well. The cells were cultured at 37° C. in an atmosphere of 5% $CO_2$ for 20-24 hours before the addition of AO3003. The cells were incubated at 37° C. in an atmosphere of 5% $CO_2$ and 19% (normoxic) oxygen for 48 hours before the cells were fixed by addition of 50 µl cold 25% Trichloroacetic acid (TCA) for 60 minutes. Cells were stored at 4° C. during fixation. TCA removed from cells and wells were washed gently ten times under running tap water. Cells dried and 50 µl 0.4% Sulphorhodamine B (SRB) added to each treatment well then the cells were incubated at room temperature for 30 minutes. SRB removed and wells were washed four times at room temperature with 1% glacial acetic acid. Cells dried and 150 µl of 10 mM Tris buffer (pH 10.5) was added to each treatment well. The plate was left on a shaking platform at room temperature for 60 minutes and the absorbance of the resulting solution was measured at 570 nm and was proportional to the cell density of the remaining cells after treatment. The results are shown in FIG. 10.

Fluorescence of AO-CHA in Pancreatic Cancer Cell Line

Figure 11:
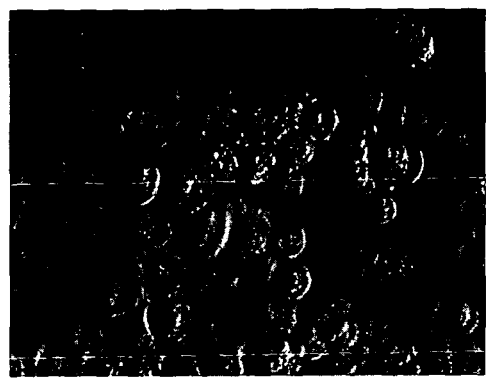
FIG. 11 shows AO-CHA fluorescence in pancreatic cancer cell line: (A) 20 μM AO-CHA, 1 h treatment of cells, brightfield, 40× magnification (B) 20 μM AO-CHA, 1 h treatment of cells, fluorescence, 40× magnification.
Figure 11:
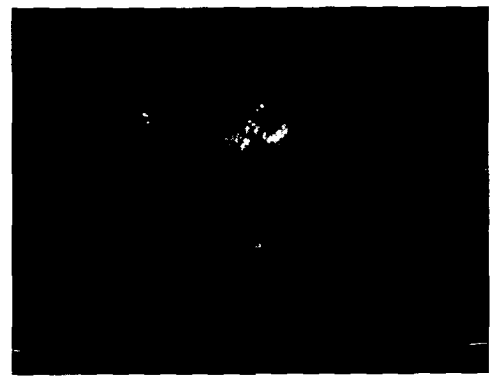

Cells were plated into a 24-well tissue culture plate at a density of $20.5 \times 10^4$ cells per well. The cells were cultured at 37° C. in an atmosphere of 5% $CO_2$ for 20-24 hours before the addition of 20 µM AO-CHA. The cells were incubated at 37° C. in an atmosphere of 5% $CO_2$ and 19% oxygen for 60 minutes. Supernatant removed and wells washed twice with PBS. Cells imaged using a fluorescence microscope using a Dapi filter and forty times magnification. Images taken for both brightfield and fluorescence. Results (FIG. 11) show effective uptake of AO-CHA into the cancer cell line.

Fluorescence of AO-3003 in Pancreatic Cancer Cell Line

Figure 12:
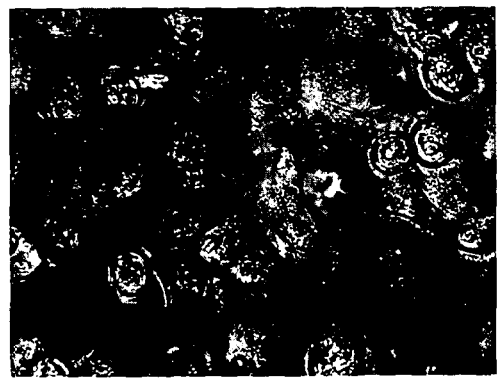
FIG. 12 shows AO-3003 fluorescence in pancreatic cancer cell line: (A) 20 μM 4 AO3003, 1 h treatment of cells, brightfield, 40× magnification (B) 20 μM AO3003, 1 h treatment of cells, fluorescence, 40× magnification
Figure 12:

Cells were plated into a 24-well tissue culture plate at a density of $18 \times 10^4$ cells per well. The Cells were cultured at 37° C. in an atmosphere of 5% $CO_2$ for 20-24 hours before the addition of 20 µM AO3003. The cells were incubated at 37° C. in an atmosphere of 5% $CO_2$ and 19% oxygen for 60 minutes. Supernatant removed and wells washed twice with PBS. Cells imaged using a fluorescence microscope using a Dapi filter and forty times magnification. Images taken for both brightfield and fluorescence. Results (FIG. 12) show effective uptake of AO-3003 into the cancer cell line.

The invention claimed is:

1. A compound of Formula I or a salt thereof:

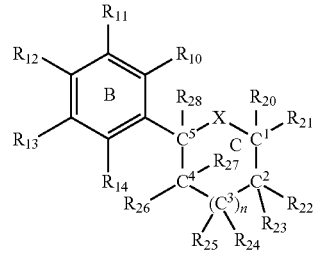

Formula I

A) X is —O—;
B) $R_{12}$ represents —OH, a glycosidic functional group or =O; $R_{26}$ represents —OH, a glycosidic functional group or together with $R_{27}$ forms =O; $R_{10}$, $R_{11}$, $R_{13}$, and $R_{14}$ each independently represent H, —OH, =O, nitro, halogen, amino, amido, cyano, carboxyl, sulphonyl, a glycosidic functional group, $C_{1-6}$ alkoxy-, hydroxy-$C_{1-6}$ alkyl-, $C_{1-6}$ alkoxy-$C_{1-6}$ alkyl-, or a saturated or unsaturated $C_{1-6}$ hydrocarbon chain which may be substituted with one or more of nitro, halogen, amino, amido, cyano, carboxyl, sulphonyl, hydroxyl, ketone or aldehyde; and wherein Ring B comprises no more than one glycosidic functional group substituent and wherein the total number of =O on Ring B is no greater than 2;
C) $R_{20}$ represents H or a 3, 4, 5, 6, 7 or 8 membered saturated or unsaturated ring;
$R_{21}$:
i) represents H; or
ii) together with $R_{22}$ provides a second bond between $C^1$ and $C^2$;
$R_{22}$:
i) represents H;
ii) together with $R_{23}$ forms =O; or
iii) together with $R_{21}$ provides a second bond between $C^1$ and $C^2$;
$R_{23}$:
i) represents H or a 3, 4, 5, 6, 7 or 8 membered saturated or unsaturated ring; or
ii) together with $R_{22}$ forms =O;
wherein at least one of $R_{20}$ and $R_{23}$ is a 3, 4, 5, 6, 7 or 8 membered saturated or unsaturated ring, wherein said ring is a saturated or unsaturated carbocycle, or a heterocycle wherein one or more available —CH— or —CH$_2$— groups present in the saturated or unsaturated ring is optionally and independently replaced by —O—, —N—, —S—, —C(O)—, —S(O)$_p$—, or —N(R$_2$)—; wherein $R_2$ and $R_3$ each independently represent H or $C_{1-8}$ alkyl, and wherein p is 1 or 2;
and
D) n is 0 or 1,
wherein when n is 0, either i) $R_{27}$ and $R_{28}$ represent H or ii) $R_{27}$ together with $R_{28}$ provide a second bond between $C^4$ and $C^5$;
or when n is 1, either i) $R_{24}$ and $R_{25}$ together form =O and $R_{27}$ and $R_{28}$ represent H or $R_{27}$ together with $R_{28}$ provide a second bond between $C^4$ and $C^5$ or $R_{26}$ and $R_{27}$ together form =O and $R_{28}$ represents H, or ii) $R_{24}$ and $R_{25}$ represent H and $R_{27}$ and $R_{28}$ represent H or $R_{27}$ together with $R_{28}$ provide a second bond between $C^4$ and $C^5$ or iii) $R_{24}$ represents H, $R_{25}$ together with $R_{27}$ provide a second bond between $C^3$ and $C^4$, $R_{26}$ represents —OH or a glycosidic functional group, and $R_{28}$ represents —OH;

and wherein the total number of =O on Ring C is no greater than 2.

2. A compound as claimed in claim 1, wherein at least one of $R_{20}$ and $R_{23}$ is a 3, 4, 5, 6, 7 or 8 membered saturated or unsaturated carbocycle.

3. A compound as claimed in claim 1, wherein at least one of $R_{20}$ and $R_{23}$ is a 5, 6, 7, or 8 membered saturated or unsaturated heterocyclic ring, having 1, 2, or 3 heteroatoms, independently selected from O, N or S.

4. A compound as claimed in claim 3, wherein said heterocylic ring is selected from pyrrolidine, tetrahydrofuran, tetrahydrothiophene, pyrazolidine, imidazolidine, thiazolidine, isoxazolidine, piperidine, piperazine, morpholine, 1,4-dioxane, thiomorpholine, 1,4-oxathiane, 1,4-dithiane, 1,3,5-thioxane, 1,3,5-trithiane, 1H-azepine, oxepine, thiepine, pyridine, pyridazine, pyrimidine, pyrazine, 1,3,5-triazine, pyrrole, furan, thiophene, pyrazole, imidazole, oxazole, isoxazole, furazan, 1,3,4-thiadiazole, thiazole, isothiazole, 1,2,3-triazole, 1,2,4-triazole and 1,2,3-oxadiazole.

5. A compound as claimed in claim 1, wherein at least one of $R_{20}$ and $R_{23}$ is a 3, 4, 5, 6, 7 or 8 membered saturated ring.

6. A compound as claimed in claim 1, wherein $R_{20}$ is a 3, 4, 5, 6, 7 or 8 membered saturated or unsaturated ring that is separated from $C^1$ by —O—, —NH— or a $C_1$-$C_6$ alkyl.

7. The compound as claimed in claim 1, wherein at lease one of $R_{20}$ and $R_{23}$ is a 3, 4, 5, 6, 7 or 8 membered saturated or unsaturated ring independently further substituted with one or more groups selected from an O-, S-, or N-containing functional group, for example, nitro, hydroxyl, carboxyl, ketone, amino, or thiol, or benzyl, phenyl, unsaturated 5, 6, 7 or 8 membered ring, cycloalkyl, cycloalkenyl, cycloalkynyl, amido, cyano, sulphonyl, aldehyde, nitrone, $C_2$-$C_6$ alkenyl, $C_2$-$C_6$ alkynyl, —NH$_2$, —F, $C_{1-6}$ alkoxy, hydroxy-$C_{1-6}$ alkyl, —CO$_2$H, —CO$_2$C$_{1-6}$alkyl, —S(O)$_2$C$_{1-6}$alkyl, —S(O)$_2$phenyl, —NO$_2$, —OH, —N(R$_2$)(R$_3$), —C(O)N(R$_2$)(R$_3$), —SC$_{1-6}$alkyl, —NHC(O)NHC$_{1-6}$ alkyl, imine and substituted or unsubstituted triphenylphosphonium.

8. The compound as claimed in claim 1, wherein $R_{20}$ is a 3, 4, 5, 6, 7 or 8 membered saturated or unsaturated ring that is separated from $C^1$ by —O—, —NH—, $C_1$-$C_6$ alkyl, —O—$C_1$-$C_6$ alkyl, —N—$C_1$-$C_6$ alkyl, $C_1$-$C_6$ alkenyl, or $C_2$-$C_6$ alkynyl.

9. The compound as claimed in claim 1, wherein the compound is:

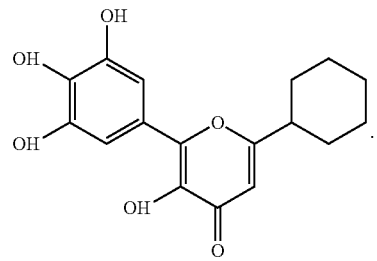 [SMILES: O=c1cc(C2CCCCC2)oc(-c2cc(O)c(O)c(O)c2)c1O]

10. The compound as claimed in claim 1, wherein the compound is:

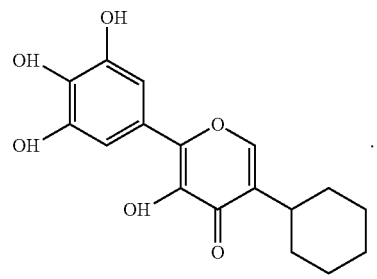 [SMILES: O=c1c(C2CCCCC2)coc(-c2cc(O)c(O)c(O)c2)c1O]

11. A composition comprising a compound as claimed in claim 1 or a pharmaceutically acceptable salt thereof and a pharmaceutically acceptable carrier, diluent, excipient or vehicle.

* * * * *